US007217700B2

(12) United States Patent
Vicari et al.

(10) Patent No.: US 7,217,700 B2
(45) Date of Patent: May 15, 2007

(54) CHEMOKINES AS ADJUVANTS OF IMMUNE RESPONSE

(75) Inventors: Alain P. Vicari, La Tour de Salvagny (FR); Christophe Caux, Bressolles (FR)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/768,917

(22) Filed: Jan. 24, 2001

(65) Prior Publication Data

US 2002/0034494 A1 Mar. 21, 2002

(51) Int. Cl.
*A61K 48/00* (2006.01)
*A61K 38/00* (2006.01)
*A61K 45/00* (2006.01)
*C12N 15/63* (2006.01)
*C07K 14/00* (2006.01)

(52) U.S. Cl. .................. 514/44; 514/2; 424/278.1; 435/320.1; 530/350

(58) Field of Classification Search ................ 530/350; 435/320.1; 514/44; 424/184.1, 199.1, 278.1
See application file for complete search history.

(56) References Cited

U.S. PATENT DOCUMENTS

2002/0071825 A1* 6/2002 Schall et al. ............... 424/85.1

FOREIGN PATENT DOCUMENTS

| EP | 0 974 357 | * | 1/2000 |
|---|---|---|---|
| EP | 0 974 357 A1 | | 1/2000 |
| WO | WO94/07521 | | 4/1994 |
| WO | WO94/13321 | | 6/1994 |
| WO | WO94/21277 | | 6/1994 |
| WO | WO95/17092 | | 6/1995 |
| WO | WO96/34891 | | 11/1996 |
| WO | WO97/19696 | | 6/1997 |
| WO | WO97/31098 | | 8/1997 |
| WO | WO97/41831 | | 11/1997 |
| WO | WO98/01557 | | 1/1998 |
| WO | WO 98/14573 | * | 4/1998 |
| WO | WO98/14573 | | 4/1998 |
| WO | WO 99/46392 | | 9/1999 |
| WO | WO 00/09151 | | 2/2000 |

OTHER PUBLICATIONS

Fayette et al. (1998) Scand. J. Immunol., vol. 48, 563-570.*
Youseff, S. et al., 2000, "CC-Chemokine-Encoding DNA Vaccines Enhance Break down of Tolerance to their Gene Products and Treat Ongoing Adjuvant Arthritis" *J. Clin. Invest.* 106:361-371.
Xin, K.Q. et al., 1999, "Immunization of RANTES Expression Plasmid with a DNA Vaccine Enhances HIV-1 Specific Immunity" *Clin. Immunol.* 92:90-96.
Sin, J. et al., 2000, "DNA Vaccines Encoding Interleukin-8 and RANTES Enhance Antigen-Specific Th1-type (CD4(+) T-cell-medicated Protective Immunity against Herpes Simplex Virus Type 2 in Vivo." *J. Virol.* 74:11173-11180.
Nomura, T. et al.; 2000, "Chemokines and Anti-cancer Immunotherapy" *Anticancer Res.* 20:4073-4080.
Lu, Y. et al., 1999, "Macrophage Inflammatory Protein 1 Alpha Expression Plasmid enhances DNA Vaccine-Induced Immune Response Against HIV-1" *Clin Exp. Immunol.* 115:335-341.
Lehner, T. et al., 2000, "Heat Shock Proteins Generate Beta-Chemokines which Function as innate adjuvants enhancing Adaptive Immunity" *Eur. J. Immunol.* 30:594-603.
Laning, J. et al., 1994, "Inhibition of in Vivo Tumor Growth by the Beta Chemokine, TCA3" *J. Immunol.* 153:4625-4635.
Kim, J.J. et al., 2000, "Chemokine Gene Adjuvants can Modulate Immune Responses Induced by DNA Vaccines" *J. Interferon Cytokine Res.* 20:487-498.
Braun, S.E. et al., 2000, "The CC Chemokine CK Beta-11/MIP-3 beta/ELC/Exodus 3 Mediates Tumor Rejection of Murine Breast Cancer Cells through NK Cells" *J. Immunol.* 164:4025-4031.
Biragyn, A. et al., "Genetic Fusion of Chemokines to Self Tumor Antigen Induces Protective, T-Cell dependent Antitumor Imunnity" *Nat. Biotechnol.* 17:253-258.
Caux et al., "Dendritic cell biology and regulation of dendritic cell trafficking by chemokines", *Springer Seminar in Immunopathology*, vol. 22, No. 4, pp. 345-369 (2000).
Dieu-Nosjean et al., "Regulation of dendritic cell trafficking: a process that involves the participation of selective chemokines", *J. Leukocyte Biology*, vol. 66, No. 2, pp. 252-262 (1999).
Kellermann et al., "The CC Chemokine Receptor-7 Ligands 6Ckine and Macrophage Inflammatory Protein-3β Are Potent Chemoattractants for In Vitro- and In Vivo- Derived Dendritic Cells", *J. Immunology*, vol. 162, No. 7, pp. 3859-3864 (1999).
Nakamura et al., "Keratinocyte-Derived Monocyte Chemoattractant Protein 1 (MCP-1): Analysis in a Transgenic Model Demonstrates MCP-1 Can Recruit Dendritic and Langerhans Cells to Skin", *J. Investigative Dermatology*, vol. 105, No. 5, pp. 635-643 (1995).
Vecchi et al., "Differential responsiveness to constitutive vs. inducible chemokines of immature and mature mouse dendritic cells", *J. Leukocyte Biology*, vol. 66, No. 3, pp. 489-494 (1999).
Xu et al., "Human recombinant monocyte chemotactic protein and other c-c chemokines bind and induce directional migration of dendritic cells in vitro", *J. Leukocyte Biology*, vol. 60, No. 3, pp. 365-371 (1996).

(Continued)

*Primary Examiner*—Anne M. Wehbe'
(74) *Attorney, Agent, or Firm*—Grant E. Reed

(57) ABSTRACT

Dendritic cells play a critical role in antigen-specific immune responses. Materials and methods are provided for treating disease states, including cancer and autoimmune disease, by facilitating or inhibiting the migration or activation of antigen-presenting dendritic cells. In particular, chemokines are used to initiate, amplify or modulate an immune response. In one embodiment, chemokines are used to attract dentritic cells to the site of antigen delivery. An increase number of dendritic at the site of antigen delivery means more antigen uptake and a modified immune response.

11 Claims, 13 Drawing Sheets

OTHER PUBLICATIONS

Zhu et al., "Human monocyte-derived dendritic cells expresing both chemotactic cytokines IL-8, MCP-1, RANTES and their receptors, and their selective migration to these chemokines", *Chinese Medical Journal (English Edition)*, vol. 113, No. 12, pp. 1124-1128 (2000).

Fioretti et al., "Reduced Tumorigenicity and Augmented Leukocyte Infiltration After Monocyte Chemotactic Protein-3 Gene Transfer" *J. Immunol.* 161(1):342-346, (1998).

Dematos et al., 1998, "Pulsing of Dentritic Cells with Cell Lysates from either B16 melanoma or MCA-106 Fibrosarcome Yields Equally Effective Vaccines Against B16 Tumors in Mice" *J Surg. Oncol.* 68(2):79-91.

Vicari et al., 2000, "Antitumor Effects of the Mouse Chemokine 6Ckine/SLC Through Angiostatic and Immunological Mechanisms" *J Immunol.* 165:1992-2000.

* cited by examiner hMCP-4 chemokine

—Nucleotide sequence (coding only)

ATGAAAGTCTCTGCAGTGCTTCTGTGCCT
GCTGCTCATGACAGCAGCTTTCAACCCCC
AGGGACTTGCTCAGCCAGATGCACTCAA
CGTCCCATCTACTTGCTGCTTCACATTTA
GCAGTAAGAAGATCTCCTTGCAGAGGCT
GAAGAGCTATGTGATCACCACCAGCAGG
TGTCCCCAGAAGGCTGTCATCTTCAGAAC
GAAACTGGGCAAGGAGATCTGTGCTGAC
CCAAAAGGAGAAGTGGGTCCAGAATTATA
TGAAACACCTGGGCCCGAAAGCTCACAC
CCTGAAGACTTGA (SEQ ID No. 11)

—Amino acid sequence (leader sequence not present in recombinant protein in italics)

*MKVSAVLLCLLLMTAAFNPQGLAQPDALNV*
PSTCCFTFSSKKISLQRLKSYVITTSRCPQK
AVIFRTKLGKEICADPKEKWVQNYMKHL
GRKAHTLKT (SEQ. No. 12)

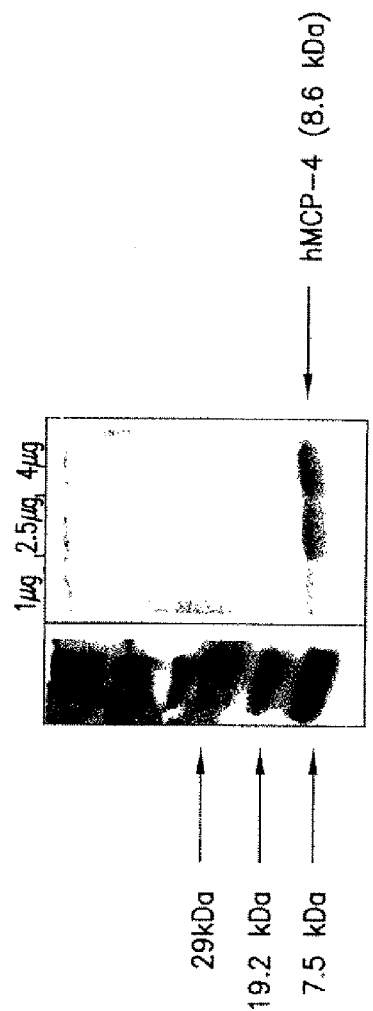

SDS-PAGE (18%) AND SILVER STAINING OF HUMAN RECOMBINANT MCP-4

FIG.3

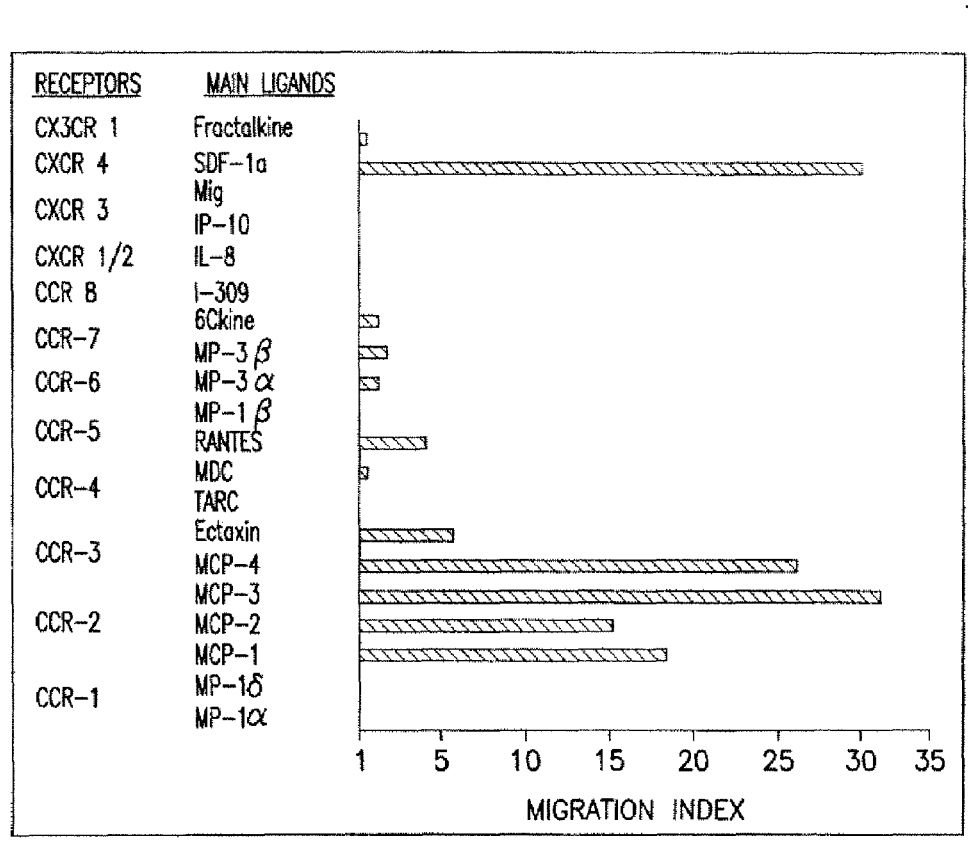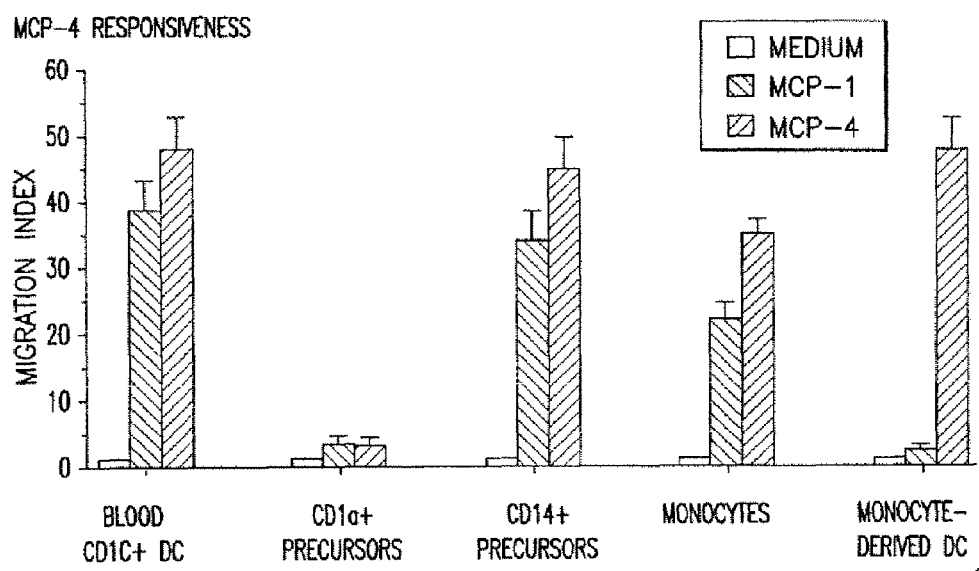
FIG.5

CHEMOKINES AS ADJUVANTS OF IMMUNE RESPONSE

FIELD OF THE INVENTION

The invention relates to the use of human chemokines in the treatment of disease states, including cancer. The administered chemokines direct the migration of either all antigen-presenting dendritic cells or a specific subset of dentritic cells. In one embodiment, disease-specific antigen(s) and/or a moiety designed to activate dentritic cells is administered in conjunction with the chemokine(s).

BACKGROUND OF THE INVENTION

Dendritic cells (DC) specialize in the uptake of antigen and their presentation to T cells. DC thus play a critical role in antigen-specific immune responses.

DC are represented by a diverse population of morphologically similar cell types distributed widely throughout the body in a variety of lymphoid and non-lymphoid tissues (Caux, et al.,1995, *Immunology Today* 16:2; Steinman, 1991, *Ann. Rev. Immunol.* 9:271–296). These cells include lymphoid DC of the spleen, and lymph nodes, Langerhans cells of the epidermis, and veiled cells in the blood circulation. DC are collectively classified as a group based on their morphology, high levels of surface MHC-class II expression as well as several accessory molecules (B7-1 [CD80] and B7-2[CD86]) that mediate T cell binding and costimulation (Inaba, et al., 1990, *Intern. Rev. Immunol.* 6:197–206; Frendenthal, et al., 1990, *Proc. Natl. Acad. Sci. USA* 87:7698), and absence of certain other surface markers expressed on T cells, B cells, monocytes, and natural killer cells.

DC are bone marrow-derived and migrate as precursors through blood stream to tissues, where they become resident cells such as Langerhans cells in the epidermis.

In the periphery, following pathogen invasion, immature DC such as fresh Langerhans cells are recruited at the site of inflammation (Kaplan, et al., 1992, *J. Exp. Med.* 175: 1717–1728; McWilliam, et al., 1994, *J. Exp. Med.* 179: 1331–1336) where they capture and process antigens, (Inaba, et al., 1986. *J. Exp. Med.* 164:605–613; Streilein, et al., 1989, *J. Immunol.* 143:3925–3933; Romani, et al., 1989., *J. Exp. Med.* 169:1169–1178; Puré, et al., 1990. J. Exp. Med. 172:1459–1469; Schuler, et al., 1985, *J. Exp. Med.* 161: 526–546).

Antigen-loaded DC then migrate from the peripheral tissue via the lymphatics to the T cell rich area of lymph nodes, where the mature DC are called interdigitating cells (IDC) (Austyn, et al., 1988, *J. Exp. Med.* 167:646–651; Kupiec-Weglinski, et al., 1988, *J. Exp. Med.* 167:632–645; Larsen, et al., 1990, *J. Exp. Med.* 172:1483–1494; Fossum, S. 1988, *Scand. J. Immunol.* 27:97–105; Macatonia, et al., 1987, *J. Exp. Med.* 166:1654–1667; Kripke, et al., 1990., *J. Immunol.* 145:2833–2838). At this site, they present the processed antigens to naive T cells and generate an antigen-specific primary T cell response (Liu, et al., 1993, *J. Exp. Med.* 177:1299–1307; Sornasse, et al., 1992, *J. Exp. Med.* 175:15–21; Heufler, et al., 1988, *J. Exp. Med.* 167:700–705).

During their migration from peripheral tissues to lymphoid organs, DC undergo a maturation process encompassing dramatic changes in phenotype and functions (Larsen, et al., 1990, *J. Exp. Med.* 172:1483–1494; Streilein, et al., 1990, *Immunol. Rev.* 117:159–184; De Smedt, et al., 1996, *J. Exp. Med.* 184:1413–1424). In particular, in contrast to immature DC such as fresh Langerhans cells, which capture and process soluble proteins efficiently and are effective at activating specific memory and effector T cells, mature DC such as IDC of lymphoid organs are poor in antigen capture and processing but markedly efficient in naive T cell priming (Inaba, et al., 1986. *J. Exp. Med.* 164:605–613; Streilein, et al., 1989, *J. Immunol.* 143:3925–3933; Romani, et al., 1989, *J. Exp. Med.* 169:1169–1178; Puré, et al., 1990, *J. Exp. Med.* 172:1459–1469; Sallusto, et al., 1995, *J. Exp. Med.* 182: 389–400; Cella, et al., 1997, *Current Opin. Immunol.* 9:10–16).

Signals regulating the traffic pattern of DC are complex and not fully understood.

Signals provided by TNFα and LPS are known to induce in vivo migration of resident DC from the tissues to the draining lymphoid organs (De Smedt, et al., 1996, *J. Exp. Med.* 184:1413–1424; MacPherson, et al., 1995, *J. Immunol.* 154:1317–1322; Roake, et al., 1995, *J. Exp. Med.* 181: 2237–2247; Cumberbatch et al., 1992, *Immunology.* 75:257–263; Cumberbatch, et al., 1995, *Immunology.* 84:31–35).

Chemokines are small molecular weight proteins that regulate leukocyte migration and activation (Oppenheim, 1993, *Adv. Exp. Med. Biol.* 351:183–186; Schall, et al., 1994, *Curr. Opin. Immunol.* 6:865–873; Rollins, 1997, *Blood* 90:909–928; Baggiolini, et al., 1994, *Adv. Immunol.* 55:97–179). They are secreted by activated leukocytes themselves, and by stromal cells including endothelial cells and epithelial cells upon inflammatory stimuli (Oppenheim, 1993, *Adv. Exp. Med. Biol.* 351:183–186; Schall, et al., 1994, *Curr. Opin. Immunol.* 6:865–873; Rollins, 1997, *Blood* 90:909–928; Baggiolini, et al., 1994, *Adv. Immunol.* 55:97–179). Responses to chemokines are mediated by seven transmembrane spanning G-protein-coupled receptors (Rollins, 1997, *Blood* 90:909–928; Premack, et al., 1996, *Nat. Med.* 2:1174–1178; Murphy, P. M. 1994, *Ann. Rev. Immunol.* 12:593–633). Several chemokines such as monocyte chemotactic protein (MCP)-3, MCP-4, macrophage inflammatory protein (MIP)-1α, MIP-1β, RANTES (regulated on activation, normal T cell expressed and secreted), SDF-1, Teck (thymus expressed chemokine) and MDC (macrophage derived chemokine) have been reported to attract DC in vitro (Sozzani, et al., 1995, *J. Immunol.* 155:3292–3295; Sozzani, et al., 1997, *J. Immunol.* 159: 1993–2000; Xu, et al., 1996, *J. Leukoc. Biol.* 60:365–371; MacPherson, et al., 1995, *J. Immunol.* 154:1317–1322; Roake, et al., 1995, *J. Exp. Med.* 181:2237–2247).

In recent years, investigators have attempted to exploit the activity of DC in the treatment of cancer. In an animal model, as few as $2 \times 10^5$ antigen-pulsed DC will induce immunity when injected into naive mice (Inaba at al., 1990, *Intern. Rev. Immunol.* 6:197–206). Flamand et al. (*Eur. J. Immunol.*, 1994, 24:605–610) pulsed mouse DC with the idiotype antigen from a B-cell lymphoma and injected them into naive mice. This treatment effectively protected the recipient mice from subsequent tumor challenges and established a state of lasting immunity. Injection of antigen alone, or B cells pulsed with antigen, had no effect, suggesting that it was the unique characteristics of DC that were responsible for the anti-tumor response. It has been postulated that DC are not only capable of inducing anti-tumor immunity, but that they are absolutely essential for this process to occur (Ostrand-Rosenberg, 1994, *Current Opinion in Immunol.* 6:722–727; Grabbe et al., 1995, *Immunol. Today* 16:117–120; Huang et al., 1994, *Science* 264:961–965). Huang and coworkers (Huang et al., 1994, *Science* 264: 961–965) inoculated mice with a B7-1 transfected tumor that was known to produce anti-tumor immunity. They demonstrated that only mice with MHC-compatible APC were capable of rejecting a tumor challenge. Studies in humans have demonstrated a similar role for DC. It has been reported that peptide-specific CTL are readily induced from purified CD8+ T cells using peptide-pulsed DC, but are not elicited when peptide-pulsed monocytes are used (Mehta-Damani et al., 1994, *J. Immunology* 153:996–1003).

Of significant clinical interest, the histologic infiltration of dendritic cells into primary tumor lesions has been associated with significantly prolonged patient survival and a reduced incidence of metastatic disease in patients with bladder, lung, esophageal, gastric and nasopharygeal carcinoma. In contrast, a comparatively poorer clinical prognosis is observed for patients with lesions that exhibit a sparse infiltration with DC and metastatic lesions are frequently deficient in DC infiltration (Becker, 1993, In Vivo 7:187; Zeid et al., 1993, *Pathology* 25:338; Furihaton et al., 1992, 61:409; Tsujitani et al., 1990, *Cancer* 66:2012; Gianni et al., 1991, *Pathol. Res. Pract.* 187:496; Murphy et al., 1993, *J. Inv. Dermatol.* 100:3358). A patient with advanced B-cell lymphoma was recently treated with DC pulsed with the patient's own tumor idiotype (Hsu et al., 1996, *Nature Medicine* 2(1):52). This produced a measurable reduction in the patient's B-cell lymphoma. Treatment of prostate cancer using DC pulsed with PSM antigen has been reported by Murphy et al. (*The Prostate* 1996 29:371).

Techniques have recently emerged for the in vitro propagation of large numbers of DC from circulating monocytes or from CD34 hematopoietic progenitors in response to granulocyte-macrophage colony stimulating factor (GM-CSF) in combination with either interleukin 4 (IL-4) or tissue necrosis factor α (TNFα) (Sallusto et al., 1994, *J. Exp. Med.* 179:1109–1118; Romani et al., 1994, *J. Exp. Med.* 180:83–93: Caux et al., 1992, *Nature* 360:258). The combination of GM-CSF and IL-4 induces peripheral blood monocytes to differentiate into potent DC (Kiertscher and Roth, 1996, *J. Leukocyte Biol.* 59:208–281). With the combination of these two cytokines a 100-fold increase in the yield of DC can be achieved from peripheral blood in vitro.

In mice, tumor antigen-loaded in vitro generated DC have been shown, by various groups, to prevent the development of tumors and more importantly to induce the regression of established tumors. A clinical trial has been conducted in which patients with melanoma are being treated with GM-CSF-activated APC pulsed with a peptide from the MAGE-1 tumor antigen (Mehta-Damani, et al., 1994, *J. Immunology* 153:996–1003). Pre-immunization, tumor-infiltrating lymphocytes from two patients were predominantly CD4+ and lacked specific tumor reactivity. In contrast, after immunization tumor infiltrating lymphocytes from the same patients were predominantly CD8+ and demonstrated MAGE-1 specific anti-tumor cytotoxicity. It thus appears from these studies that DC have a unique and potent capacity to stimulate immune responses.

Dendritic cell therapy thus represents a very promising approach to the treatment of disease, in particular, cancer. There is a continuing need for improved materials and methods that can be used not only to expand and activate antigen presenting dendritic cells, but to facilitate the migration of DC so as to be both therapeutically as well as prophylactically useful.

SUMMARY OF THE INVENTION

The present invention fulfills the foregoing need by providing materials and methods for treating disease states by facilitating or inhibiting the migration or activation of antigen-presenting dendritic cells. It has now been discovered that chemokines are useful therapeutic agents. Disease states which can be treated in accordance with the invention include parasitic infections, bacterial infections, viral infections, fungal infections, cancer, autoimmune diseases, graft rejection and allergy.

The invention provides a method of treating disease states comprising administering to an individual in need thereof an amount of chemokine sufficient to increase the migration of immature dendritic cells to the site of antigen delivery. In one aspect of the invention a chemokine such as MCP-1, MCP-2, MCP-3, MCP-4, MIP-1α, MIP-3α, RANTES, SDF-1, Teck, DC tactin-β, 6Ckine, MDC, MIP-5 or a combination thereof is administered. In a preferred method of the invention, a disease-associated antigen, such as a tumor-associated antigen is administered in conjunction with the chemokine.

Another aspect of the invention provides a method of treating disease states comprising administering to an individual in need thereof an amount of chemokine sufficient to decrease the migration of immature dendritic cells to the site of antigen delivery.

In still another aspect of the invention, cytokines, in particular GM-CSF and IL-4 are administered in combination, either before or concurrently, with the chemokine. Administration of GM-CSF and IL-4 stimulates generation of DC from precursors, thereby increasing the number of DC available to capture and process antigen.

Yet another aspect of the invention an activating agent such as TNF-α, IFN-α RANK-L or agonists of RANK, and agonists of the toll-like receptor family of molecules is administered to provide maturation signals which drives the migration of DC from tissues toward lymphoid organs through the draining lymph.

The present invention also provides a method of enhancing an immune response in a mammal comprising administering chemokine MCP-4 or a biologically active fragment of MCP-4 to a mammal. Human MCP-4 (hMCP-4) is active on human blood dendritic cells, recruiting dendritic cells and dendritic cell precursors from blood. In a preferred aspect, the chemokine is recombinant. Most preferably, the chemokine is administered with antigen, for instance, in the form of a fusion protein of recombinant chemokine and antigen. Such antigens can be tumor associated, bacterial, viral or fungal.

Additionally, the present invention provides a method of enhancing an immune response in a mammal comprising administering chemokine 6Ckine or a biologically active fragment of 6Ckine to a mammal. Human 6Ckine is active on human blood dendritic cells, recruiting dendritic cells and dendritic cell precursors from blood. By virtue of recruiting dendritic cells, chemokine 6Ckine acts as an anti-tumor agent, and specifically is shown to exert an angiostatic effect on tumor vasculature. In a preferred aspect, the chemokine is recombinant. Most preferably, the chemokine is administered with antigen, for instance, in the form of a fusion protein of recombinant chemokine and antigen. Such antigens can be tumor associated, bacterial, viral or fungal.

In still another aspect of the invention, cytokines, in particular GM-CSF and IL-4 are administered in combination, either before or concurrently, with the chemokine.

In a final aspect, the invention provides fusion proteins comprising MCP-4 or a biologically active portion of MCP-4 and antigen and 6Ckine or a biologically active portion of 6Ckine and antigen. These fusion proteins can be administered to a mammal in the form of a plasmid, viral vector or in the form of a recombinant vector.

BRIEF DESCRIPTION OF THE DRAWINGS

FIG. 3 shows the nucleotide and partial amino acid sequence of chemokine hMCP-4.

FIG. 5 shows that hMCP-4 is active in recruiting dendritic cells in human blood.

DETAILED DESCRIPTION OF THE INVENTION

Figure 1:
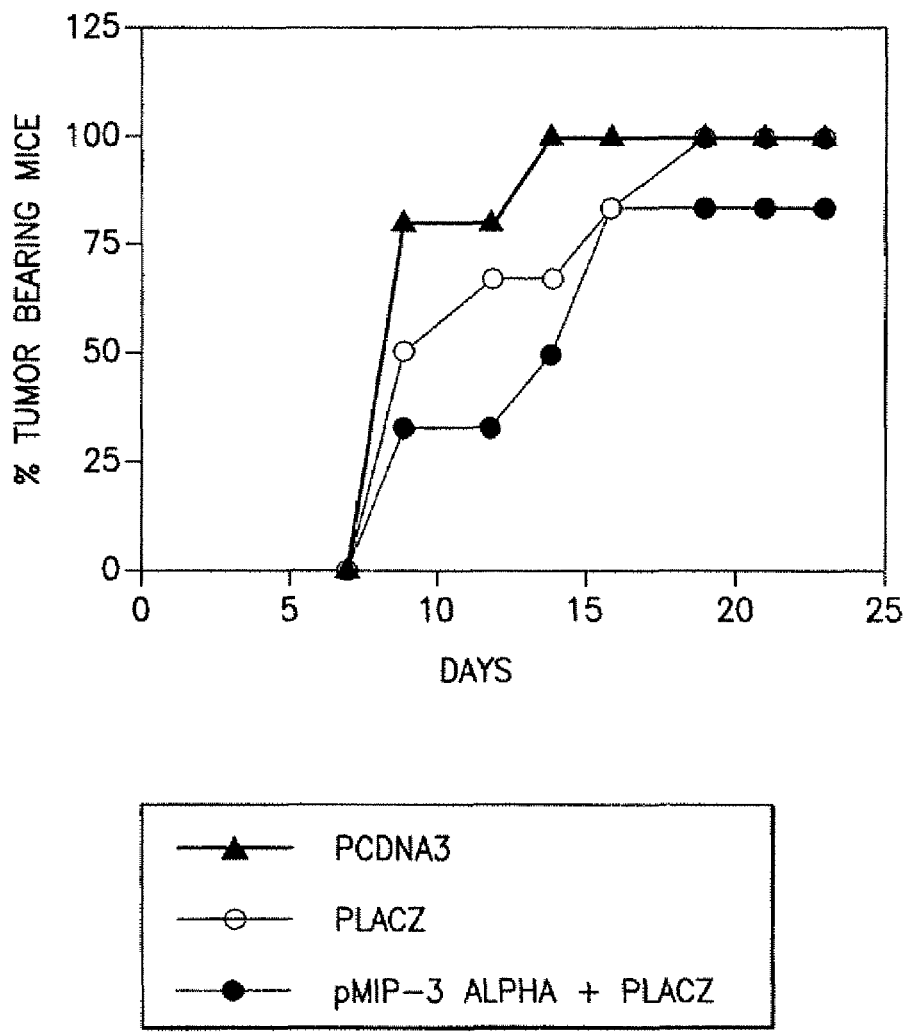
FIG. 1 shows that immunization with a plasmid containing MIP-3α and a tumor associated antigen has a protective effect against tumor engraftment.

All references cited herein are incorporated in their entirety by reference.

The relation between signals inducing DC migration in vivo and their responses to chemokines was heretofore not known. The inventors have discovered that the pattern of chemokine receptors expressed by DC change according to their stage of maturation and that chemokines can be used to drive migration of DC subsets and thereby control the initiation of the immune response. Chemokines can be used in accordance with the invention as adjuvants to attract selectively the immature DC subsets at the site of antigen delivery. In the context of autoimmune disease, tissue rejection or allergy, the invention provides a method of blocking DC functions by interfering with their migration through e.g., the development of CCR6, CCR7, and CCR2 agonists and antagonists.

Depending on the subset of DC presenting the antigen to the immune system, the response could vary dramatically. DC can induce tolerance. DC found in the medulla of the thymus play a role in the negative selection of developing self-reactive thymocytes (Brocker, et al., 1997, *J. Exp. Med.* 185(3):541–550). DC can also tolerize self-reactive peripheral T cells (Kurts, et al., 1997, *J. Exp. Med.* 186(2):239–245; Adler, et al., 1998, *J. Exp. Med.* 187(10):1555–1564). A specific subset of mouse DC, possibly of lymphoid origin, has been proposed to induce immune tolerance (Ardavin, 1993, *Nature* 362(6422):761–763). Furthermore, the recent description that the candidate human counterpart to the lymphoid DC (the DC-2) (Grouard, et al., 1997, *J. Exp. Med.* 185(6):1101–1111) cannot secrete IL-12 suggests that, following presentation by this subpopulation, the immune response might be biased towards a TH-2 type.

When the goal is to decrease the immune response, tolerizing DC (autoimmunity, allergy) are recruited, or the quality of the response is modified by recruiting specifically DC-2 (TH1 greater that TH2, i.e., in allergy).

A chemokine for use in the invention is a natural protein of the body that is active on a restricted subset of DC, in particular, immature DC. Several of these chemokines, including, but not limited to, MIP-3α, Teck, MDC and MCP-4, and 6Ckine have been identified by the inventors.

The chemokine used in practicing the invention may be a recombinant protein with an amino-acid sequence identical to the natural product, or a recombinant protein derived from the natural product but including modifications that changes its pharmacokinetic properties while keeping its original chemoattractant property. The mode of delivery of the chemokine may be by injection, including intradermal, intramuscular and subcutaneous, or topical, such as an ointment or a patch.

The chemokine may also be delivered as a nucleic acid sequence by the way of a vector, such as a viral vector (e.g., adenovirus, poxvirus, retrovirus, lentivirus), or an engineered plasmid DNA.

The term "chemokine" as used herein includes chemotactic agents. A chemotactic agent may be a small chemical compound which is a selective agonist of a chemokine receptor expressed by immature DC. CCR6, the natural receptor of the chemokine MIP-3α is an example of such a receptor.

In a particularly preferred embodiment of the invention, the chemokine is administered with a disease-associated antigen. The antigen can be any molecular moiety against which an increase or decrease in immune response is sought. This includes antigens derived from organisms known to cause diseases in man or animal such as bacteria, viruses, parasites (e.g., *Leishmania*) and fungi. This also includes antigens expressed by tumors (tumor-associated antigens) and plant antigens (allergens).

Tumor associated antigens for use in the invention include, but are not limited to Melan-A, tyrosinase, p97, β-HCG, GalNAc, MAGE-1, MAGE-2, MAGE-3, MAGE-4, MAGE-12, MART-1, MUC1, MUC2, MUC3, MUC4, MUC18, CEA, DDC, melanoma antigen gp75, HKer 8, high molecular weight melanoma antigen, K19, Tyr1 and Tyr2, members of the pMel 17 gene family, c-Met, PSA, PSM, α-fetoprotein, thyroperoxidase, gp100, NY-ESO-1, telomerase and p53. This list is not intended to be exhaustive, but merely exemplary of the types of antigen which may be used in the practice of the invention.

Different combinations of antigens may be used that show optimal function with different ethnic groups, sex, geographic distributions, and stage of disease. In one embodiment of the invention at least two or more different antigens are administered in conjunction with the administration of chemokine.

The antigen can by delivered or administered at the same site and the same time as the chemokine, or after a delay not exceeding 48 hours. Concurrent or combined administration, as used herein means the chemokine and antigen are administered to the subject either (a) simultaneously in time, or (b) at different times during the course of a common treatment schedule. In the latter case, the two compounds are administered sufficiently close in time to achieve the intended effect. The antigen can be in the form of a protein, or one or several peptides, or of a nucleic acid sequence included in a delivery vector.

Both primary and metastatic cancer can be treated in accordance with the invention. Types of cancers which can be treated include but are not limited to melanoma, breast, pancreatic, colon, lung, glioma, hepatocellular, endometrial, gastric, intestinal, renal, prostate, thyroid, ovarian, testicular, liver, head and neck, colorectal, esophagus, stomach, eye, bladder, glioblastoma, and metastatic carcinomas. The term "carcinoma" refers to malignancies of epithelial or endocrine tissues including respiratory system carcinomas, gastrointestinal system carcinomas, genitourinary system carcinomas, prostatic carcinomas, endocrine system carcinomas, and melanomas. Metastatic, as this term is used herein, is defined as the spread of tumor to a site distant to from the primary tumor including regional lymph nodes.

A moiety designed to activate, induce or stimulate maturity of the DC may be advantageously administered. Such agents provide maturation signals which promote migration from the tissues to the lymph nodes. This moiety can be a natural product of the body such as TNF-α or RP-105, or an agonist antibody recognizing a specific structure on DC such as an anti-CD-40 antibody, or another substance. The activating substance can be a sequence of nucleic acids containing unmethylated CpG motifs or agonist of a toll-like receptor known to stimulate DC. In the embodiment of the invention where the chemokine and/or antigen is delivered by the means of a plasmid vector, these nucleic acid sequences may be part of the vector.

GM-CSF and IL-4 can advantageous be administered in combination with the chemokine and/or antigen. The administration combination of GM-CSF and IL-4 stimulates generation of DC from precursors. GM-CSF and IL-4 may be administered for purposes of increasing the number of circulating immature DC which might then be locally recruited locally be the subsequent injection of chemokine(s). This protocol would imply a systemic pre-treatment for a least five to seven days with GM-CSF and IL-4. An alternative would be to favor by local administration of GM-CSF and IL-4 the local differentiation of DC-precursors (monocytes) into immature DC which could then pick up the antigen delivered at the same site.

Generally, chemokine(s) and/or antigen(s) and/or activating agent(s) and/or cytokine(s) are administered as pharmaceutical compositions comprising an effective amount of chemokine(s) and/or antigen(s) and/or activating agent(s) and/or cytokine(s) in a pharmaceutical carrier. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. A pharmaceutical carrier can be any compatible, non-toxic substance suitable for delivering the compositions of the invention to a patient.

The quantities of reagents necessary for effective therapy will depend upon many different factors, including means of administration, target site, physiological state of the patient, and other medicants administered. Thus, treatment dosages should be titrated to optimize safety and efficacy. Animal testing of effective doses for treatment of particular cancers will provide further predictive indication of human dosage. Various considerations are described, e.g., in Gilman et al. (eds.) (1990) *Goodman and Gilman's: The Pharmacological Bases of Therapeutics,* 8th Ed., Pergamon Press; and *Remington's Pharmaceutical Sciences,* 17th ed. (1990), Mack Publishing Co., Easton, Pa. Methods for administration are discussed therein and below, e.g., for intravenous, intraperitoneal, or intramuscular administration, transdermal diffusion, and others. Pharmaceutically acceptable carriers will include water, saline, buffers, and other compounds described, e.g., in the *Merck Index,* Merck & Co., Rahway, N.J. Slow release formulations, or a slow release apparatus may be used for continuous administration.

Dosage ranges for chemokine(s) and/or antigen(s) and/or activating agent(s) would ordinarily be expected to be in amounts lower than 1 mM concentrations, typically less than about 10 μM concentrations, usually less than about 100 nM, preferably less than about 10 pM (picomolar), and most preferably less than about 1 fM (femtomolar), with an appropriate carrier. Generally, treatment is initiated with smaller dosages which are less than the optimum dose of the compound. Thereafter, the dosage is increased by small increments until the optimum effect under the circumstance is reached. Determination of the proper dosage and administration regime for a particular situation is within the skill of the art.

The preferred biologically active dose of GM-CSF and IL-4 in the practice of the claimed invention is that dosing combination which will induce maximum increase in the number of circulating $CD14^+/CD13^+$ precursor cells; the expression of antigen presenting molecules on the surface of DC precursors and mature DC; antigen presenting activity to T cells; and/or stimulation of antigen-dependent T cell response consistent with mature DC function. In the practice of the invention the amount of IL-4 to be used for subcutaneously administration typically ranges from about 0.05 to about 8.0 μg/kg/day, preferably 0.25–6.0 μg/kg/day, most preferably 0.50–4.0 μg/kg/day. The amount of GM-CSF is to be used for subcutaneous administration typically ranges from about 0.25 μg/kg/day to about 10.0 μg/kg/day, preferably from about 1.0–8.0 μg/kg/day, most preferably 2.5–5.0 μg/kg/day. An effective amount for a particular patient can be established by measuring a significant change in one or more of the parameters indicated above.

It has been found that the administration of chemokine MCP-4 or a biologically active fragment of MCP-4 promotes the recruitment of dendritic cells in vivo in the mouse in a dose-dependent manner and is also active on human dendritic cells isolated from blood. Biologically active fragment means a portion of the MCP-4 molecule which is sufficient to stimulate a measurable immune response. This response can be measured as an enhanced antigen specific stimulation of immunoglobulin levels in serum, typically known as a B-cell response. In addition, a biologically active fragment of MCP-4 will stimulate the production of certain classes of immunoglobulins such as IgG2a that require an increase in T Cells. In addition, a biologically active fragment of MCP-4 will enhance an antigen-specific anti-tumor response. An enhanced response could be measured by a slower tumor growth or lower tumor incidence following challenge with a tumor expressing the antigen. An enhanced immune response could also be measured by analyzing the antigen-specific cytotoxic response of defined populations of lymphocytes (blood, spleen, lymph nodes, tumor). Of course, it is recognized that small molecules that are CCR2 agonists (e.g., found by drug discovery screen) would also enhance the antigen-specific anti-tumor response. The rationale is that all MCPs (1–4) are natural CCR2 agonists, and subsequently an artificial, small molecule agonist may have the same effect. Many current therapeutics are small molecules obtained by organic chemistry synthesis.

Preferred embodiments consist of but are not restricted to recombinant hMCP-4 protein alone or combined with substances allowing for its slow release at delivering site (depot); fusions proteins consisting of hMCP-4 or fraction of hMCP-4 and an antigen (peptide more than 9 amino acids or protein); DNA or viral vector encoding for hMCP-4 or fraction of hMCP-4 with or without an antigen (peptide more than 9 amino acids or protein), or a nucleic acid sequence included in a delivery vector.

Human MCP-4 (hMCP-4) belongs to the CC family of chemokines. Its sequence was first published in 1996. (Uguccioni et al., 1996, Monocyte Chemotactic Protein 4 (MCP-4), A Novel Structural and Functional Analogue of MCP-3 and Eotaxin, *J. Exp. Med.* 183:2379–2394). Human MCP-4 is a peptide of 8.6 kDa that consists of 75 amino acid residues. (FIG. 3.) It is also known as CK-β-10, SCY-A13 and NCC-1 (Swiss-Prot accession number Q99616) and was renamed CCL13 in the new chemokine nomenclature. (Zlotnik et al., 2000, Chemokines: A New Classification System and Their Role In Immunity, *Immunity,* 12:121–127).

6Ckine belongs to the CC family of chemokines (Hedrick, et al., 1997, *J. Immunol.* 159: 1589–1593.) It is also known as CK-β-9, exodus-2 and SLC (Swiss-Prot accession number O00585 for human protein) and was renamed CCL21. Human 6Ckine (h6Ckine) binds to the chemokine CCR7 while mouse 6Ckine (m6Ckine) binds to CCR7 as well as to the CXCR3 receptor, although with a lower affinity (Jenh, et al., 1999, *J. Immunol.* 162: 3765–3769.) Mouse 6Ckine has been shown to have anti-tumor effect when injected into tumors in mice (Sharma, et al., 2000, *J. Immunol.* 164: 4558–4563.)

6Ckine like MIP-3β and MCP-4 induces the migration of mature DC. Interestingly, 6Ckine, as well as MIP-3β can induce the migration of all human DC populations after maturation, including CD1a+ Langerhans cells, CD14+ interstitial DC, monocyte-derived DC, circulating blood CD11c+ DC, monocytes, and circulating blood CD11c– plasmacytoid DC. The response to 6Ckine is observed after maturation induced by several DC activators, including CD40-L, TNF-α, and LPS. As seen in the case of MIP-3β, CCR7 is up-regulated during DC activation, via 6Ckine, likely explaining the response to 6Ckine.

It is therefore proposed that the chemokine h6Ckine could be used in cancer treatment. Preferred embodiments consist of but are not restricted to: recombinant h6Ckine protein alone or combined with substances allowing for its slow release at delivering site (depot at tumor site); fusion proteins or constructs made by chemical ligation consisting of h6Ckine or fraction of h6Ckine and a targeting moiety allowing delivery of the construct into tumors (e.g., antibody or fragment of antibody, protein ligand, peptide of more than 10 amino acids); DNA or viral vector (e.g., adenovirus) encoding for h6Ckine or fraction of h6Ckine with or without a targeting moiety as described above.

EXAMPLES

The invention can be illustrated by way of the following non-limiting examples, which can be more easily understood by reference to the following materials and methods.

Hematopoietic factors, reagents and cell lines. Recombinant GM-CSF (specific activity: $2.10^6$ U/mg, Schering-Plough Research Institute, Kenilworth, N.J.) was used at a saturating concentration of 100 ng/ml. Recombinant human TNFα (specific activity: $2 \times 10^7$ U/mg, Genzyme, Boston, Mass.) was used at an optimal concentration of 2.5 ng/m. Recombinant human SCF (specific activity: $4 \times 10^5$ U/mg, R&D Abington, UK ) was used at an optimal concentration of 25 ng/ml. Recombinant human IL-4 (specific activity: $2.10^7$ U/mg, Schering-Plough Research Institute, Kenilworth, N.J.) was used at a saturating concentration of 50 U/ml. Recombinant human chemokines MIP-1α (specific activity: $2 \times 10^5$ U/mg, $9 \times 10^{12}$ U/M), RANTES (specific activity: $1 \times 10^4$ U/mg, $8 \times 10^{10}$ U/M), MIP-3α (specific activity: $4 \times 10^5$ U/mg, $3 \times 10^{12}$ U/M) and MIP-3β (specific activity: $1 \times 10^4$ U/mg, $9 \times 10^{10}$ U/M) were obtained through R&D (Abington, UK). LPS was used at 10 ng/ml (Sigma).

The murine CD40 ligand transfected cell line (CD40-L L cells) was used as a stimulator of DC maturation.

Generation of DC from cord blood CD34$^+$ HPC. Umbilical cord blood samples were obtained following full term delivery. Cells bearing CD34$^+$ antigen were isolated from mononuclear fractions through positive selection as described (Caux, et al., 1996, *J. Exp. Med.* 184:695–706; Caux, et al., 1990, *Blood.* 75:2292–2298), using anti-CD34$^+$ monoclonal antibody (Immu-133.3, Immunotech Marseille, France), goat anti mouse IgG coated microbeads (Miltenyi Biotec GmBH, Bergish Gladbach, Germany) and Minimacs separation columns (Miltenyi Biotec). In all experiments the isolated cells were 80% to 99% CD34$^+$. After purification, CD34$^+$ cells were cryopreserved in 10% DMSO.

Cultures were established in the presence of SCF, GM-CSF and TNFα as described (Caux, et al., 1996, *J. Exp. Med.* 184:695–706) in endotoxin-free medium consisting of RPMI 1640 (Gibco, Grand Island, N.Y.) supplemented with 10% (v/v) heat-inactivated fetal bovine serum (FBS) (Life Techniques, France, Irvine, UK), 10 mM Hepes, 2 mM L-glutamine, $5 \times 10^{-5}$ M β-mercaptoethanol, 100 µg/ml gentamicin (Schering-Plough, Levallois, France) (referred to as complete medium). After thawing, CD34$^+$ cells were seeded for expansion in 25 to 75 cm$^2$ culture vessels (Linbro, ICN Biomedicals, Acron, Ohio) at $2 \times 10^4$ cells/ml. Optimal conditions were maintained by splitting these cultures at day 5 and 10 with medium containing fresh GM-CSF and TNFα (cell concentration: $1-3 \times 10^5$ cells/ml). At day 12, between 70 to 90% of the cells are CD1a$^+$ DC.

Isolation of immature and mature DC according to CD86 expression by FACS-sorting. After 12 days of culture in presence of GM-CSF and TNFα, cells were collected and labeled with FITC-conjugated OKT6 (CD1a) (Ortho Diagnosis System, Raritan, N.J.) and PE-conjugated IT2.2 (CD86) (Pharmingen, San Diego, Calif.). Cells were separated according to CD1a and CD86 expression into immature CD1a$^+$CD86$^-$, and mature CD1a$^+$CD86$^+$ DC populations using a FACStarplus® (laser setting: power 250 mW, excitation wavelength 488 nm, Becton-Dickinson, Sunnyvale, Calif.). All the procedures of staining and sorting were performed in presence of 0.5 mM EDTA in order to avoid cell aggregation. Reanalysis of the sorted populations showed a purity >98%.

Generation of DC from peripheral blood monocytes. Monocytes were purified by immunomagnetic depletion (Dynabeads, Dynal Oslo, Norway) after preparation of PBMC followed by a 52% Percoll gradient. The depletion was performed with anti-CD3 (OKT3), anti-CD19 (4G2), anti-CD8 (OKT8), anti-CD56 (NKH1, Coulter Corporation, Hialeah, Fla.) and anti-CD16 (ION16, Immunotech) monoclonal antibodies. Monocyte-derived dendritic cells were produced by culturing purified monocytes for 6–7 days in the presence of GM-CSF and IL-4 (Sallusto, et al., 1994, *J. Exp. Med.* 179:1109–1118).

Induction of maturation of in vitro generated DC. CD34$^+$ HPC were cultured until day 6 in presence of GM-CSF+ TNFα and in presence of GM-CSF alone from day 6 to day 12 in order to preserve their immaturity. Immature DC from CD34+ HPC or monocyte-derived DC were activated for 3 h to 72 h in presence of TNFα (2.5 ng/ml) or LPS (10 ng/ml) or CD40L transfected L cells (1 L cells for 5 DC) as described (Caux, et al., 1994, *J. Exp. Med.* 180:1263–1272).

Purification of CD11c+ DC from peripheral blood or tonsils. CD11c+ DC were prepared as previously described from peripheral blood or tonsils (Grouard, et al., 1996, *Nature* 384:364–367). Briefly, tonsils obtained from children undergoing tonsillectomy were finely minced and digested with collagenase IV and DNase I (Sigma). The collected cells were centrifuged through Ficoll-Hypaque with SRBC (BioMérieux, Lyon, France) for 15 min at 500 rpm, then for 30 min at 2000 rpm. Peripheral blood mononuclear cells (PBMC) were isolated by Ficoll-Hypaque. CD3+ T cells (OKT3), CD19+ B cells (4G7), and CD14+ monocytes (MOP9) were removed from the resulting low density cells by magnetic beads (anti-mouse Ig-coated Dynabeads, Dynal). A second depletion was performed with anti-NKH1, anti-glycophorine A (Immunotech) and anti-CD20 (1F54). The remaining cells were stained with the following mAbs: anti-CD1a FITC (OKT6); anti-CD14 FITC, anti-CD57 FITC, anti-CD16 FITC, anti-CD7 FITC, anti-CD20 FITC, anti-CD3 FITC (Becton Dickinson, Mountain View, Calif.); anti-CD4 PE-Cy5 (Immunotech) and anti-CD11c PE (Becton Dickinson). CD4+CD11c+lineage− DC were isolated by cell sorting using a FACStarPlus® (laser setting: power 250 mW, excitation wavelength 488 nm). All the procedures of depletion, staining and sorting were performed in presence of 0.5 mM EDTA. Reanalysis of the sorted population showed a purity >97%.

Chemotaxis assay. Cell migration was evaluated using a chemotaxis microchamber technique (48-well Boyden microchamber, Neuroprobe, Pleasanton, Calif.) (Bacon, et al., 1988, *Br. J. Pharmacol.* 95:966–974). Briefly, human recombinant MIP-3α and MIP-3β, MIP-1α and RANTES were diluted to concentrations ranging from 1 ng/ml to 1000 ng/ml in RPMI 1640 medium, and were added to the lower wells of the chemotaxis chamber. $10^5$ cells/well (or $5\times10^4$ cells/well for CD11c+ DC) in 50 µl of RPMI 1640 medium were applied to the upper wells of the chamber, with a standard 5-µm pore polyvinylpyrrolidone-free polycarbonate filter (Neuroprobe) separating the lower wells. The chamber was incubated at 37° C. in humidified air with 5% $CO_2$ for 1 h. Then, cells which had migrated to the underside of the filter were stained with Field's A and Field's B (BDH, Dorcet, England) and counted using an image analyzer (software: Vision Explorer and ETC 3000, Graphtek, Mirmande, France) in two randomly selected low power fields (magnification×20). Each assay was performed in duplicate and the results were expressed as the mean±SD of migrating cells per 2 fields.

Extraction of total RNA and Synthesis of cDNA. Cells were prepared as described above, and total RNA was extracted by the guanidinium thiocyanate method as mentioned by the manufacturer (RNAgents total RNA isolation system, Promega). After DNAse I (RQ1 RNAse free DNAse, Promega) treatment, RNA was quantified by spectrophotometry and the quality was evaluated by electrophoresis in formaldehyde denaturing conditions. First strand cDNA was synthesized from total RNA extracted in RNAse-free conditions. The reaction was performed with 5 µg of total RNA, 25 ng/µl oligo $dT_{12-18}$ primers (Pharmacia, Orsay, France) and the Superscript kit (SuperScript II RNase H− Reverse Transcripase, Gibco BRL), as described by the manufacturer. For all samples, synthesis of cDNA was controlled and calibrated by RT-PCR using β-actin primers for 21 cycles.

RT RT-PCR analysis. Semi-quantitative PCR was performed in a Perkin Elmer 9600 thermal cycler, in a final volume of 100 µl reaction mixture containing 2.5 U Ampli-Taq enzyme (5 U/µl, Perkin Elmer, Paris, France) with its 1× buffer, 0.2 mM of each dNTP (Perkin Elmer, Paris, France), 5% DMSO, and 1 µM of each forward and reverse primers. CCR6 (Accession No. Z79784) and CCR7 (Accession No. L08176) primers were designed within regions of lowest homology between the chemokine receptors. +80/CCR6 5'-ATTLCAGCGATGTTTTCGACTC-3' (SEQ ID NO: 1) forward primer, −1081/CCR6 5'-GGAGAAGCCTGAG-GACTTGTA-3' (SEQ ID NO: 2) reverse primer, +154/CCR7 5'-GATIACATCGGAGACAACACC-3' (SEQ ID NO: 3) forward primer and −1202/CCR7 5'-TAGTCCAG-GCAGAAGAGTCG-3' (SEQ ID NO: 4) reverse primer were used for RT-PCR and sequencing. For both chemokine receptors, the reaction mixture was subjected to 30 and 35 cycles of PCR with the following conditions: 94° C. for 1 mm 61.5° C. for 2 mm and 72° C. for 3 mm. PCR products were visualized on 1.2% agarose gels containing 0.5 µg/ml ethidium bromide. Reaction products migrating at the predicted size (1,021 bp for CCR6 and 1,067 bp for CCR7) were gel purified and subcloned into pCRII TA cloning vector (Invitrogen, Leek, The Netherlands) for sequencing verification on an ABI 373A Sequencer (Applied Biosystems, Foster City, Calif.) using dye terminator technology. Two other oligonucleotides, −622/CCR6 5'-GCTGCCT-TGGGTGTTGTATTT-3' (SEQ ID NO: 5) and +662/CCR7 5'-AGAGGAGCAGCAGTGAGCAA-3' (SEQ ID NO: 6), were used as probes for hybridization with the PCR products separated on 1.2% agarose gel and blotted onto Hybond $N_+$ membranes (Amersham, Les Ulis, France).

Calcium fluorimetry. Intracellular $Ca^{2+}$ concentration was measured using the fluorescent probe Indo-1, according to the technique reported by Grynkiewicz et al. (*J. Biol. Chem.*, 1985, 260:3440–3450) Briefly, cells were washed in PBS and resuspended at $10^7$ cells/ml in complete RPMI 1640 medium (see above). Then, cells were incubated for 45 min at room temperature with 3 µg/ml Indo-1 AM (Molecular Probes) in the dark. After incubation, cells were washed and resuspended in HBSS/1% FCS at $10^7$ cells/ml. Before measurement of intracellular $Ca^{2+}$ concentration, cells were diluted 10 fold in HBSS/10 mM Hepes/1.6 mM $CaCl_2$ preheated at 39° C. Samples were excited at 330 nm with continuous stirring and the Indo-1 fluorescence was measured as a function of time at 405 nm (dye is complexed with $Ca^{2+}$) and 485 nm ($Ca^{2+}$-free medium), in a 810 Photomultiplier Detection System (software: Felix, Photon Technology International, Monmouth Junction, N.J.). Results are expressed as the ratio of values obtained at the two emission wavelengths.

In situ hybridization. In situ hybridization was performed as described (Peuchmaur, et at., 1990, *Am. J. Pathol.* 136: 383–390). Two couple primers were used for amplifying by RT-PCR the majority of the open reading frame of MIP-3α (Accession No. D86955)and MIP-3βα (Accession No. U77180) genes.

+77/MIP-3α 5'-TTGCTCCTGGCTGCTTTG-3' (SEQ ID NO: 7) forward primer and

−425/MIP-3α 5'-ACCCTCCATGATGTGCAAG-3' (SEQ ID NO: 8) reverse primer, +25/MIP-3β 5'-CTGCTG-GTTCTCTGGACTTC-3' (SEQ ID NO: 9) forward primer and −439/MIP-3β 5'-CACACTCACACTCACACACAC-3' (SEQ ID NO: 10) reverse primer, were used as described above with an annealing temperature at 62° C. Then, PCR products were cloned into pCRII TA cloning vector (Invitrogen, Leek, The Netherlands) for the generation of sense and anti-sense probes with the adapted promoters. Sense and antisense $^{35}$S-labeled probes of MIP-3α and MIP-3β, were obtained by run off transcription of the 367 bp and 435 bp fragments, respectively. Six μm human tonsil sections were fixed in acetone and 4% paraformaldehyde followed by 0.1 M triethanolamine/0.25% acetic anhydride. The sections were hybridized overnight, RNAse A treated and exposed for 24 days. After development sections were stained with hematoxylin.

Example 1

Differential Responsiveness to MIP-3α and MIP-3β During Development of CD34$^+$-derived DC To understand the regulation of DC traffic the response to various chemokines of DC at different stages of maturation was studied. DC were generated from CD34$^+$ HPC cultured in the presence of GM-CSF+ TNFα, and tested at different days of culture for their ability to migrate in response to chemokines in Boyden microchambers. MIP-3α and MIP-3β recruited 2 to 3 times more CD34$^+$-derived DC than MIP-1α or RANTES. However, MIP-3α and MIP-3β attracted DC collected at different time points of the culture. The response to MIP-3α was already detected at day 4, maximal at day 5–6 and lasted until day 10. At day 13 to 14, the response to MIP-3α was usually lost. In contrast, the response to MIP-3β, which could not be detected before day 10, peaked at day 13, and persisted beyond day 15. Of note, at early time points, when most of the cells in culture were still DC precursors (CD1a$^-$CD86$^-$), the response to MIP-3α could be detected at concentrations of 1 to 10 ng/ml (depending on the experiment). In contrast, four days later, when almost all cells were immature DC (CD1a$^+$CD86$^-$), ≧300 ng/ml were needed to attract the cells, suggesting a progressive desensitization of the cells during maturation. Relatively high concentrations of MIP-3β (300 ng/ml) were also needed to recruit mature DC (CD1a$^+$CD86$^+$). Checkerboard analysis established that MIP-3α and MIP-3β induced chemotaxis and not chemokinesis of DC.

To confirm the relation between the stage of maturation and the response to MIP-3α and MIP-3β, CD34$^+$-derived DC were sorted by FACS at day 10 of culture according to CD86 expression into immature DC (CD1a$^+$CD86$^-$) and mature DC (CD1a$^+$CD86$^+$). CD1a$^+$CD86$^-$ responded exclusively to MIP-3α while CD1a$^+$CD86$^+$ responded mainly to MIP-3β. These observations also confirmed that the cells recruited by MIP-3α and MIP-3β were indeed DC (CD1a$^+$). The correlation between DC maturation and chemokine responsiveness was further illustrated when the immaturity of DC was preserved by removing TNFα from day 6 to day 12 and when their maturation was synchronized by addition of TNFα, LPS or CD40L. Response to MIP-3α had strongly decreased upon 48 h maturation with TNFα, LPS and CD40L. Meanwhile, the response to MIP-3β was induced by all three signals, CD40L and LPS being more potent than TNFα. In kinetics experiments, the response to MIP-3α decreased by 50 to 70% after only 24 h of CD40 activation and was completely lost at 72 h. The response to MIP-3β was already maximal after 24 h of CD40 activation and required relatively high concentration of chemokine (100–300 ng/ml at 48 h).

Taken together, these results establish that immature CD34$^+$-derived DC respond to MIP-3α while mature DC respond to MIP-3β.

Example 2

Responses to MIP-3α and MIP-3β Parallel the Expression of Their Respective Receptors CCR6 and CCR7 on CD34$^+$-derived DC To define the mechanisms of regulation of MIP-3α and MIP-3β responsiveness, the expression of their respective receptors CCR6 (Power, et al., 1997, *J. Exp. Med.* 186: 825–835; Greaves, et al., 1997, *J. Exp. Med.* 186:837–844; Baba, et al., 1997, *J. Biol. Chem.* 272:14893–14898; Liao, et al., 1997, *Biochem. Biophys. Res. Commun.* 236:212–217) and CCR7 (Yoshida, et al., 199, *J. Biol. Chem.* 272:13803–13809) mRNA was studied by semi-quantitative RT-PCR. During DC development from CD34$^+$ HPC, CCR6 mRNA was first detected at day 6, increased up to day 10 after when it decreased and became barely detectable at day 14. In contrast, CCR7 mRNA appeared at day 10 and steadily increased up to day 14. Moreover, CD40L-dependent maturation induced progressive down-regulation of CCR6 mRNA which became almost undetectable after 72 h, and up-regulation of CCR7 mRNA as early as 24 h. Similar results were obtained after either LPS or TNFα-induced DC maturation. The up-regulation of CCR7 mRNA following activation was confirmed by Southern blot analysis of cDNA libraries.

In line with the migration assays, and the regulation of CCR6 and CCR7 expression, MIP-3α induced a Ca$^{2+}$ flux exclusively in resting/immature DC and MIP-3β in mature DC only. Maximal Ca$^{2+}$ fluxes were observed with 30 ng/ml of MIP-3α and 30 ng/ml of MIP-3β, on immature and mature DC, respectively.

These results show that changes in responsiveness to MIP-3α and MIP-3β are linked to the regulation of CCR6 and CCR7 mRNA expression, and suggest that CCR6 and CCR7 are the major functional receptors expressed on DC for MIP-3α and MIP-3β, respectively.

Example 3

The Response to MIP-3β is also Induced upon Maturation of Monocyte-derived DC

Monocyte-derived DC, generated by culturing monocytes in presence of GM-CSF+IL-4 for 6 days, are typically immature DC (CD1a$^+$, CD14$^-$, CD80$^{low}$, CD86$^{low}$, CD83$^-$) (Cella, et al., 1997, *Current Opin. Immunol.* 9:10–16; Sallusto, et al., 1994, *J. Exp. Med.* 179:1109–1118). They migrated in response to MIP-1α and RANTES but neither to MIP-3α nor to MIP-3β. The lack of response of monocyte-derived DC to MIP-3α is in accordance with the absence of CCR6 expression on those cells (Power, et al., 1997, *J. Exp. Med.* 186:825–835; Greaves, et al., 1997, *J. Exp. Med.* 186:837–844). Upon maturation induced by TNFα, LPS, or CD40L, responses to MIP-1α and RANTES were lost while response to MIP-3β was induced. Like with CD34$^+$-derived DC, the response to MIP-3β correlated with the up-regulation of CCR7 mRNA expression observed upon maturation induced by TNFα, LPS or CD40L. Again, up-regulation of CCR7 occurred at early time points (3 h), after TNFR or CD40 signaling. Moreover, migration and chemokine receptor expression data were in agreement with $Ca^{2+}$ flux results.

These results extend to monocyte-derived DC the concept that upon maturation, DC loose their responsiveness to various chemokines while they become sensitive to a single chemokine, MIP-3β.

Example 4

Peripheral Blood CD11c+ DC Migrate in Response to MIP-3β After Maturation

The chemotactic activities of MIP-3α and MIP-3β on immature CD11c+ DC isolated from peripheral blood (or tonsils) also were studied. Freshly isolated DC did not migrate in response to MIP-3α, nor to MIP-3β, an observation which correlates with the absence of CCR6 and CCR7 mRNA expression in these cells. However, the maturation which is known to occur after overnight culture with GM-CSF, turned on the response of CD11c+ DC to MIP-3β but not to MIP-3α. Once more, the response to MIP-3β correlated with the induction of CCR7 mRNA expression.

Therefore, even though immature CD11c+ DC freshly isolated from blood cannot respond to MIP-3α, these results show that the maturation dependent on responsiveness to MIP-3β also applies to ex-vivo isolated DC.

Example 5

In vivo MIP-3α is Expressed in Inflamed Epithelium and MIP-3β within T Cell Rich Areas of Tonsils The physiological relevance of the findings reported in Example 4 was addressed through the analysis of MIP-3α and MIP-3β mRNA expressions by in situ hybridization on sections of inflamed tonsils. mRNA for MIP-3α was detected at high levels in inflamed epithelial crypts but not in T cell rich areas nor in B cell follicles. In fact, MIP-3α expression was restricted to cells lining the epithelial crypts. In contrast, expression of MIP-3β mRNA was restricted to T cell rich areas. The strongest signal was present in scattered cells, with a distribution overlapping that of IDC. Outside the paracortical area, no signal could be detected in B cell follicles, nor in epithelial crypts. Serial sections showed clear absence of MIP-3β expression within epithelial crypts where MIP-3α was abundantly present. Sense probes for MIP-3α and MIP-3β, did not generate background hybridization.

Therefore, MIP-3α expression is restricted to inflamed epithelium, at the site of antigen entry where immature DC should be recruited. In contrast, MIP-3α is only detected in paracortical areas, where mature IDC home and generate primary T cell responses.

Example 6

Chemokine MIP-3α Administration in an In vitro Mouse Model

Since MIP-3α was shown by the inventors to be a chemotactic factor for mouse immature dendritic cells in vitro, the ability of the chemokine MIP-3α to attract immature DC in vivo and to modulate the antigen-specific immune response against a tumor in vivo was studied. If a tumor-associated antigen is delivered at the same time, more DC will be available to capture the antigen, and therefore the antigen-specific response against this antigen should be increased.

Chemokine was delivered in vivo via a plasmid vector (pcDNA3, InVitrogen), that contains the cDNA encoding mouse MIP-3α under the control of the CMV promoter (PMIP-3α). The antigen used was β-galactosidase isolated from E. coli. The antigen was delivered in vivo via the same plasmid vector pcDNA3 (called pLacz). The tumor was a C26 colon carcinoma syngeneic in BALB/c mice that has been stably transfected with the gene encoding for β-galactosidase. Therefore, in this system, β-galactosidase defines a tumor-associated antigen.

Groups of 6 female 6 week-old mice were injected with either the empty pcDNA3 plasmid (negative control), the plasmid pLacz encoding the antigen alone, or a mixture of pLacz and PMIP-3α. Injections (50 μg of total plasmid) were performed in the hind footpad every week for 4 weeks. After that time, mice were injected subcutaneously with the C26 tumor cell line expressing β-galactosidase. Typically, all mice develop subcutaneous tumors after 10 days. The appearance of tumors in these groups of mice were monitored. It was found that the appearance of tumors was delayed after pLacz and pLacz+PMIP-α injection. (FIG. 1) This shows that immunization with a plasmid encoding a tumor-associated antigen has a protective effect against tumor engraftment. The delay was greater with pLacz+ PMIP-3α than with pLacz, suggesting that the chemokine MIP-3α increases the tumor associated antigen-specific immune response when delivered with the antigen.

Figure 2:
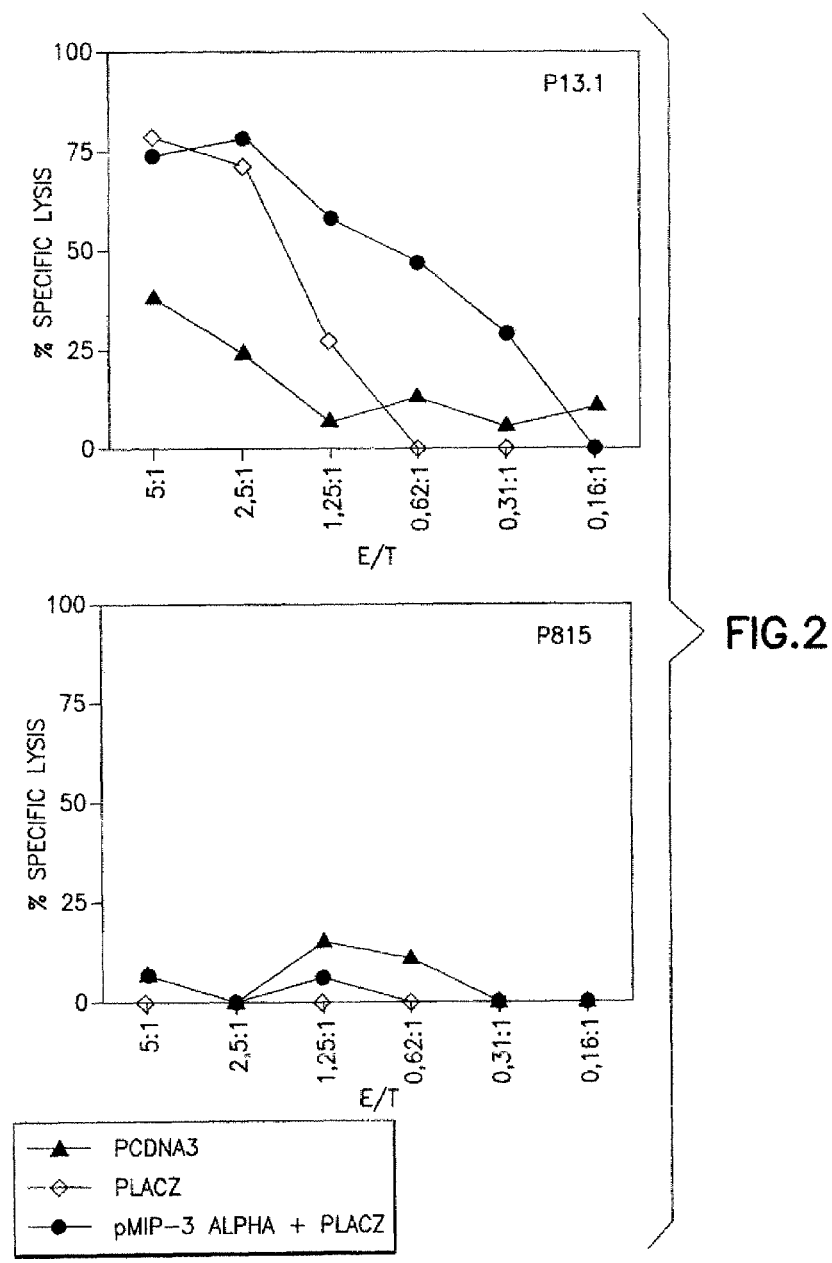
FIG. 2 shows greater CTL activity with the administration of chemokine MIP-3α.

It is believed that a good anti-tumor response is associated with a strong T cell-mediated antigen-specific cytotoxicity (CTL activity). Therefore, the CTL activity in the same groups of mice was analyzed 30 days after tumor inoculation. Spleen cells were removed and stimulated for five days with irradiated syngeneic DC plus an immunodominant CTL peptide derived from β-galactosidase in the presence of interleukin-2. Then their ability to lyse a cell line stably transfected with the gene encoding for β-galactosidase (P13.1) was measured, in parallel with their ability to lyse the parental cell line P815 that does not express β-galactosidase. (FIG. 2) This was done using different ratios of effectors (splenocytes) versus targets (P13.1 or P815). The results show that mice injected with pLacz+P-MIP-3α prior to tumor challenge have a greater CTL activity than mice injected only with pLacz or with PCDNA3 alone, against the tumor-associated antigen β-galactosidase.

Example 7

Chemokine hMCP-4 Administration in an In vivo Mouse Model

Figures 4A, 4B:
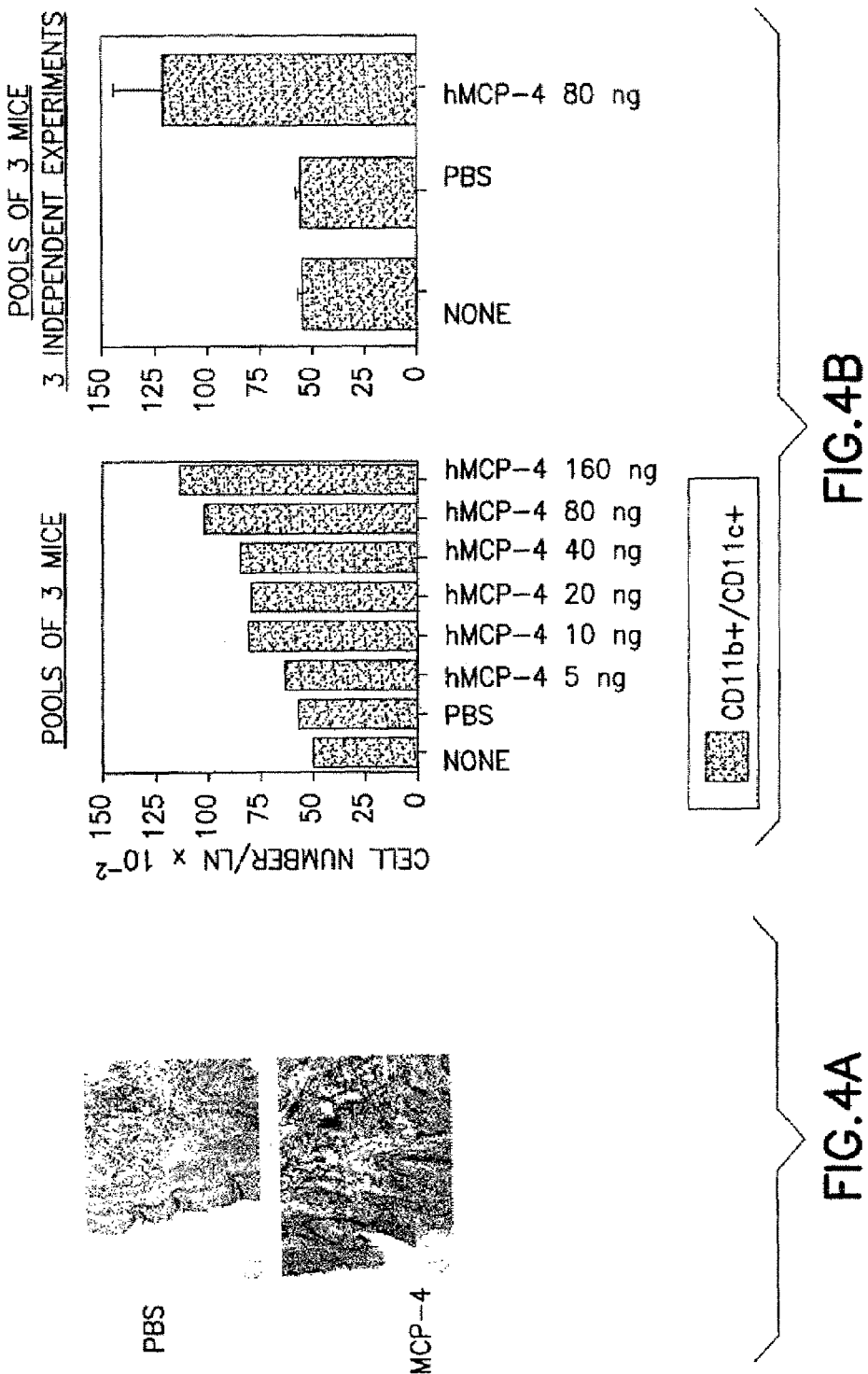
FIG. 4(A+B) shows that hMCP-4 injection promotes the recruitment of dendritic cells in vivo in the mouse in a dose-dependent manner.

The inventors have shown that hMCP-4 local injection can promote the recruitment of dendritic cells in vivo in the mouse in a dose-dependent manner. (FIG. 4)

6- to 10-week-old female BALB/c mice were purchased from Charles River (Iffa-Credo, L'Arbresle, France) and maintained in our facilities under standard conditions. Procedures involving animals and their care were conducted in conformity with EEC (European Economic Community) Council Directive 86/609, OJL 358, 1, Dec. 12, 1987. Recombinant human MCP-4 protein, >97% pure (FIG. 3), was obtained from Peprotech and resuspended in PBS (Gibco-BRL). Groups of three mice were injected with PBS alone or varying amounts of human MCP-4 in PBS, intracutaneously in the right hind footpad under a 50 μ volume.

Mice were sacrificed after 2 or 20 hours and the skin at the site of injection as well as the popliteal lymph node, draining the injection site, removed. Local cell recruitment in the skin was examined by immuno-histochemistry with specific monoclonal antibodies according to standard techniques. Cell suspensions were prepared from lymph nodes in RPMI 1640+10% fetal calf serum (FCS) (Gibco-BRL). Cell were numerated and stained in PBS+2% FCS with biotin-CD11c and FITC-CD11b antibodies (Becton Dickinson), followed by PE-streptavidin (Dako), according to standard procedures. Expression of CD11b and CD11c, that define populations of mouse dendritic cells, was analyzed on a Facscan flow cytometer (Becton Dickinson) using the CellQuest software. From this analysis and numeration, the number of CD11b+CD11c+ in each lymph node was determined. These experiments show (A) that local injection of hMCP-4 is able to induce the recruitment of cells expressing CD11b at the site of injection after a short period (2 hours). These cells could be mouse blood dendritic cells or dendritic cell precursors such as monocytes, since both can express CD11b. In the mouse, no circulating blood dendritic cells have been identified, due to limitations in techniques. In humans, however, blood dendritic cells can be isolated and they respond in chemotaxis assays to hMCP-4 (FIG. 3). (B) In the draining lymph node, where antigen-specific immune responses are initiated, hMCP-4 induces the recruitment of dendritic cells identified by the co-expression of CD11b and CD11c, but only after a longer period (20 hours). This delay most likely corresponds to the maturation and migration time necessary for dendritic cells or their precursors, initially recruited in the skin, in order to migrate to the draining lymph node.

Example 8

Response of Dendritic Cells Derived from Human Blood to hMCP-4 hMCP-4 is also active on human dendritic cells, including dendritic cells isolated from blood. (FIG. 5)

Panel A: Human circulating blood CD11c+ DC were enriched by magnetic bead depletion, and studied in transwell (5 μm pore size) migration assay, in response to various chemokines. The migration was revealed after 2 hours by triple staining: lineage markers FITC, HLA-DR tricolor, and CD11c PE, and analyzed by Facs. Each chemokine was tested over a wide range of concentrations (1 to 1000 ng/ml) and only the optimal response is shown. Results are expressed as migration index and represent the mean values obtained from 3 to 10 independent experiments. Blood CD11c+ mainly respond to MCP-4 as well as to MCP1, 2 and 3 (not shown). SDF-1, lacking selectivity, being the only other chemokine strongly active on CD11c+ DC.

Panel B: Different human DC and DC precursor populations including blood CD11c+ DC, monocytes, monocyte-derived DC, CD1a+ Langerhans cell precursors and CD14+ interstitial DC precursors were studied in transwell (5 μm pore size) migration assay, in response to MCP-1 and MCP-4. All populations respond to MCP-4 except CD1a+ Langerhans cell precursors. In addition monocyte-derived DC respond to MCP-4 but not to MCP-1, through a receptor different from CCR2.

Importantly MCP-4 is active on human DC. In particular, compared to other chemokines MCP-4 is the most potent chemokine inducing the migration of circulating blood CD11c+ DC. MCP-1, and MCP-2 and MCP-3 display a similar activity on blood DC. The MCPs likely recruit blood DC through CCR2 which is highly expressed on these cells. In addition, MCP-4 is active on all DC or DC precursors populations (blood CD11c+DC, monocytes, monocyte-derived DC, CD14+ interstitial type DC precursors) except the CD1a+ Langerhans cell precursors which do not express CCR2. Finally MCP-4, but not MCP-1 induces the migration of monocyte derived DC, likely through a receptor different from CCR2.

Example 9 hMCP-4 and β-galactosidase Administration in an In vivo Mouse Model

Furthermore, hMCP-4 can be used as adjuvant of an antigen-specific immune response induced by plasmid DNA vaccination. In addition, when hMCP-4 is used as adjuvant of plasmid DNA vaccination, it can increase the protection of mice subsequently challenged with a tumor expressing the antigen encoded by the plasmid DNA.

Groups of seven 6 to 8 week-old female BALB/c mice (Iffa-Credo, L'Arbresle, France) were injected with PBS alone or 100 ng of human MCP-4 in PBS, intracutaneously in the right hind footpad under a 50 μl volume. After three hours, mice were injected at the same site with 50 μg of control pcDNA3 plasmid (InVitrogen) or 50 μg of pcDNA3 plasmid encoding for beta-galactosidase under the CMV promoter (pLacz, InVitrogen), under a 50 μl volume of PBS. This immunization protocol was repeated four times at one week interval.

Serum was collected one day before the first immunization and one week after the last immunization. Levels of beta-galactosidase specific immunoglobulins in serum were measured with specific ELISA assays as previously described (Mendoza et al., 1997, *J. Immunol.* 159:5777–5781).

Figure 6:
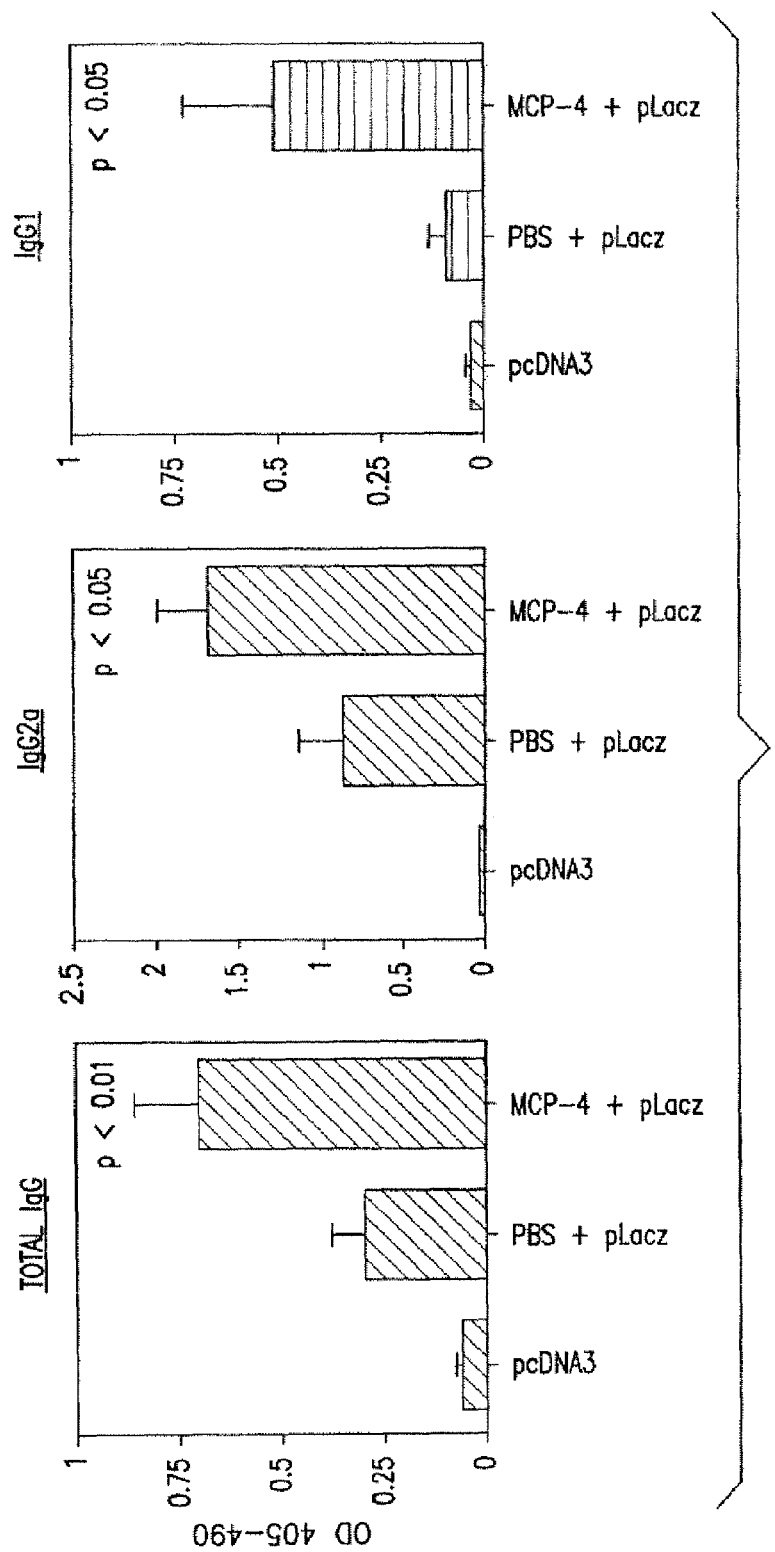
FIG. 6 shows that MCP-4 injection increases the antigen-specific humoral response following beta-galactosidase DNA immunization.

As seen in FIG. 6, MCP-4 injection increases the antigen-specific humoral response following beta-galactosidase DNA immunization (50 micrograms DNA injection 3 hours after 100 ng hMCP-4 injection in rear right footpad). FIG. 6 shows anti-betagalactosidase antibodies measured after 4 immunizations [significance hMCP-4+pLacz compared with PBS+pLacz: Student's test.]

One week after the last immunization, groups of mice were challenged with a subcutaneous injection in the right flank of $5 \times 10^4$ C26-BAG colon carcinoma cells which express beta-galactosidase (a kind gift from Mario Colombo, Instituto Nazionale Tumori, Milan, Italy), under a 100 μl volume of RPMI-1640. The onset of tumors was appraised three times a week by palpation.

Figure 7:
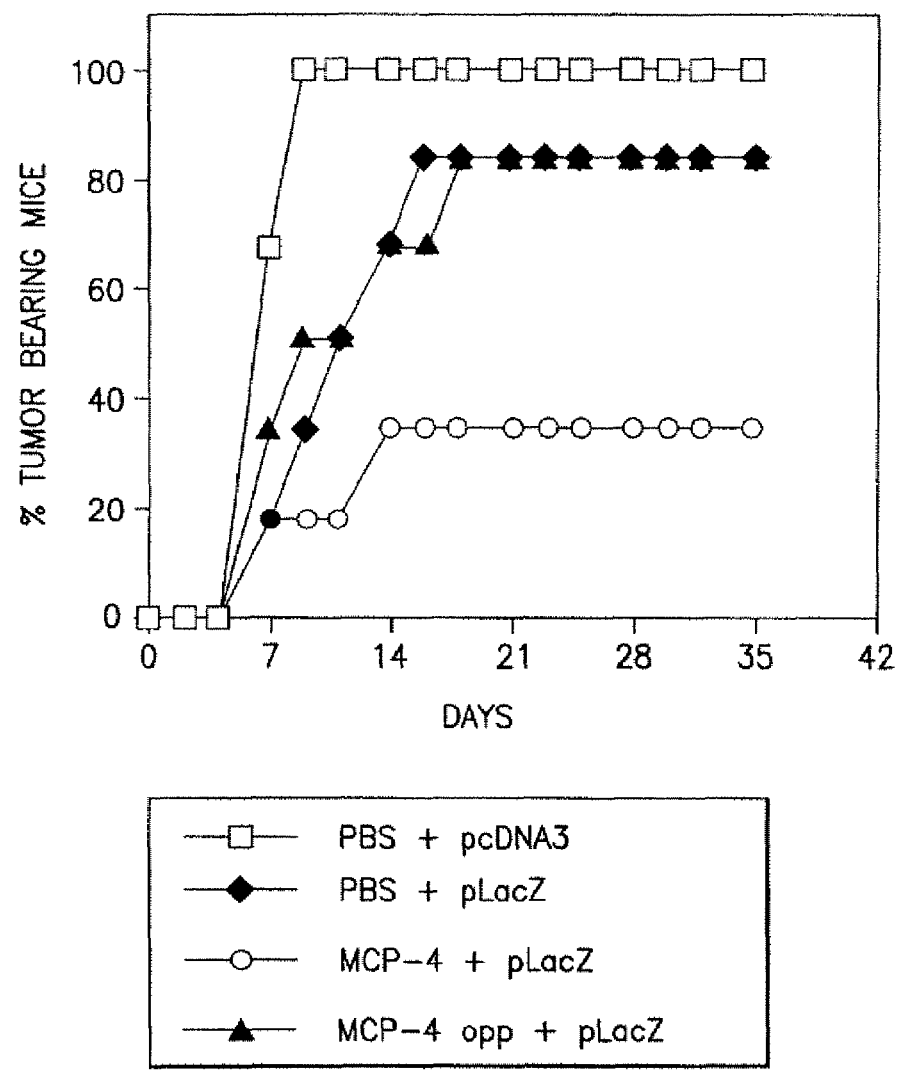
FIG. 7 shows that MCP-4 increases the anti-tumor effect induced by beta-galactosidase DNA immunization when mice are challenged with a C26 colon carcinoma cell line that expresses beta-galactosidase.

As seen in FIG. 7, MCP-4 injection increases the anti-tumor effect induced by beta-galactosidase DNA immunization (50 micrograms DNA injection 3 hours after 100 ng hMCP-4 injection in rear right footpad, four immunizations prior to tumor challenge) when mice are challenged with a C26 colon carcinoma cell line that expresses beta-galactosidase [significance hMCP-4 +pLacz compared with PBS+pLacz: p<0.05 logrank MCP-4 opp: hMCP-4 injected at distant site.]

Examples 7–9 thus indicate that the chemokine hMCP-4 can be used as adjuvant of immune responses, in particular anti-tumor responses. The enhanced immune response as mediated by MCP-4 administration has been measured as enhanced antigen-specific immunoglobulin levels in serum. Thus, there is clearly an enhancement of B cell responses to MCP-4 administration. In addition, since there is an increase in subclasses of immunoglobulins such as IgG2a, that require T Cell mediated help for switch, it is likely that there is an increase in T Cell mediated responses as well.

Example 10

Response of Human Dendritic Cells to h6Ckine Chemokine

Figure 8:
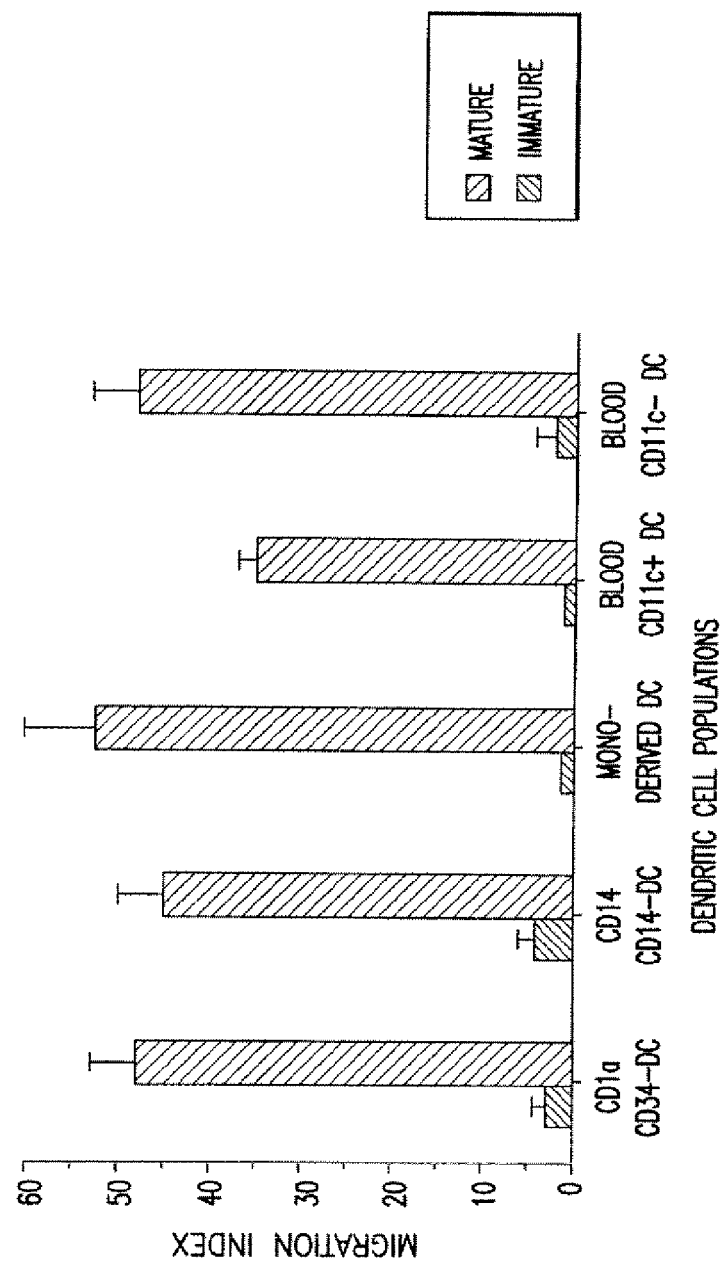
FIG. 8 shows that h6Ckine is active in recruiting dendritic cells in human blood.

In this example, the inventors have shown that human 6Ckine (h6Ckine) is a chemotactic factor for all known subsets of dendritic cells in man, in vitro. In particular, h6Ckine is active on human blood dendritic cells following a short 3 hour incubation with GM-CSF, IL-3 and CD40L. (FIG. 8)

Different human DC populations including CD1a+ Langerhans cell, CD14+ interstitial DC, monocyte-derived DC, circulating blood CD11c+ DC, monocytes, and circulating blood CD11c– plasmacytoid DC were studied in migration assay, in response to human 6Ckine before and after maturation. CD34-derived DC precursors were isolated by Facs-sorting according to CD1a and CD14 expression after 6 days of culture in presence of GM-CSF+TNF and SCF. Cells were cultured until day 12 in GM-CSF alone (immature) or GM-CSF+CD40-L (mature) for the last two days. Monocyte-derived DC were generated by culturing monocytes in presence of GM-CSF+IL-4 for 5 days and activated (mature) or not (immature) with CD40-L for the last 2 days. Human circulating blood CD11c+ DC and CD11c– plasmacytoid DC were enriched by magnetic bead depletion, and facs-sorted using triple staining into lineage markers FITC negative, HLA-DR tricolor positive, and CD11c PE positive and negative. CD11c+ DC and CD11c– plasmacytoid DC were cultured for three hours in presence of GM-CSF+IL-3 with (mature) or without (immature) CD40-L. Migration assays were carried out during 1 to 3 hours using 5 or 8 µm pore size Transwell (6.5 mm diameter, COSTAR, Cambridge, Mass.), and revealed by facs analysis. All populations respond to 6Ckine but only after CD40-L activation.

Example 11

Chemokine m6Ckine Gene Transfer in Tumor Models

Figure 9A:
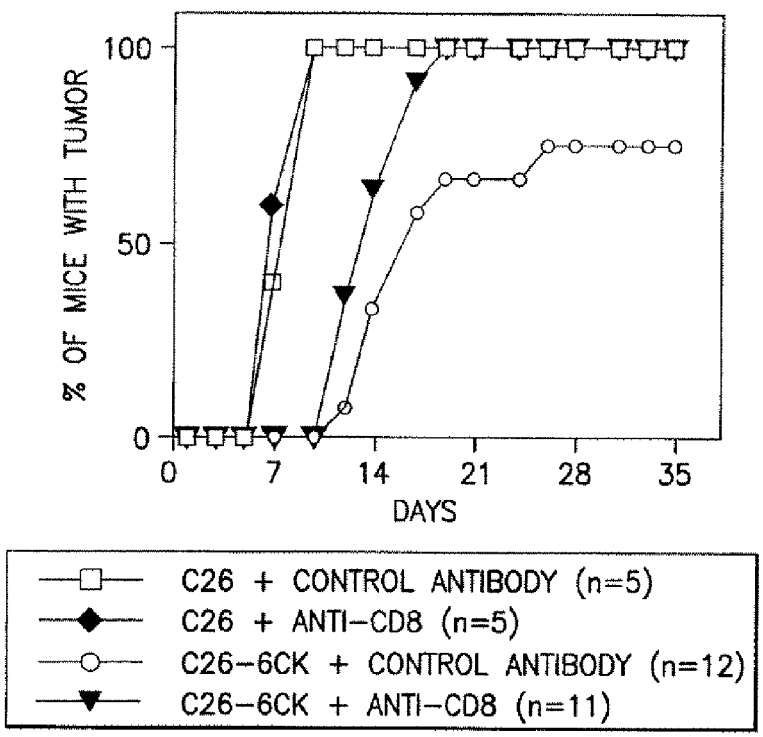
FIG. 9(A+B) shows that C26 colon carcinoma tumor cells engineered to express m6Ckine are less tumorigenic and that this effect depends on CD8+ cells and Natural Killer cell activity, in vivo.
Figure 9B:
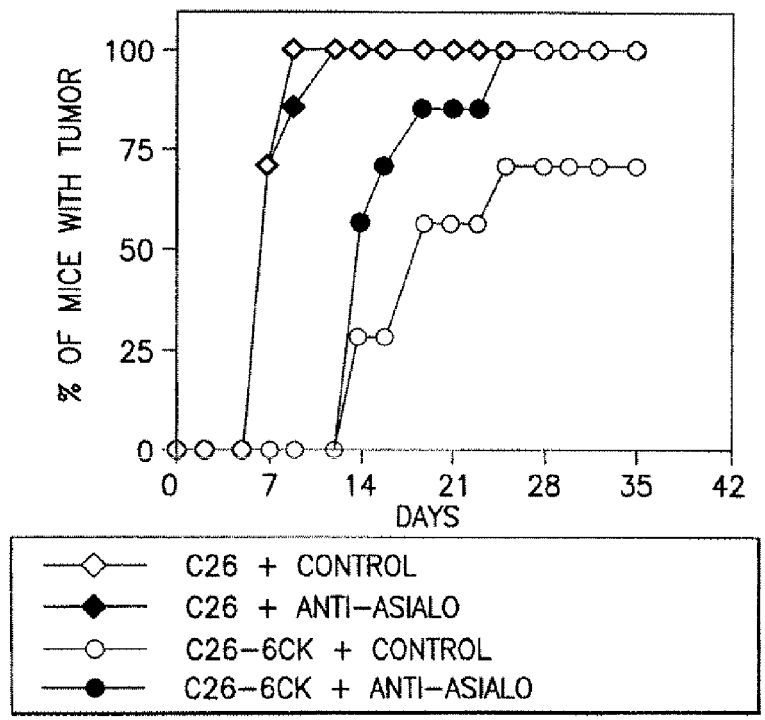

In this example, the inventors have shown that:

C26 colon carcinoma tumor cells engineered to express m6Ckine are less tumorigenic and that this effect depends on CD8+ cells and Natural Killer cell activity, in vivo. (FIG. 9);

C26 tumors expressing m6Ckine are significantly infiltrated by dendritic cells and CD8+T cells compared with parental tumors. (FIG. 10); and C26 colon carcinoma tumor cells engineered to express m6Ckine are less angiogenic than the parental C26 tumor. (FIG. 11)

Figure 10:
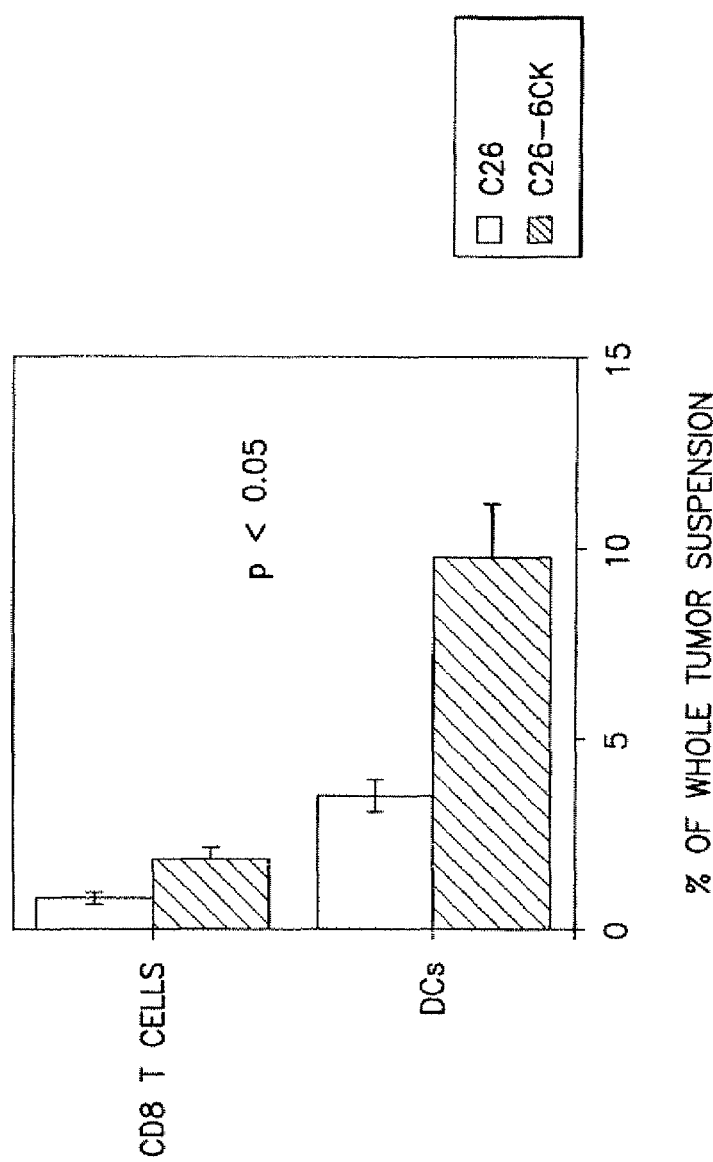
FIG. 10 shows that C26 tumors expressing m6Ckine are significantly infiltrated by dendritic cells and CD8+ T cells compared with parental tumors.

6- to 10-week-old female BALB/c (H-$2^d$) mice were purchased from Charles River (Iffa-Credo, L'Arbresle, France) and maintained under standard conditions. Procedures involving animals and their care were conducted in conformity with EEC (European Economic Community) Council Directive 861609, OJL 358, 1, Dec. 12, 1987. All tumor cell cultures were performed in DMEM (Gibco-BRL, Life Technologies, Paisley Park, Scotland) supplemented with 10% FCS (Gibco-BRL), 1 mM hepes (Gibco-BRL), Gentallin (Schering-Plough, Union, N.J.), $2\times10^{-5}$ M beta-2 mercaptoethanol (Sigma, St Louis, Mo.). All cell cultures were performed at 37° C. in a humidified incubator with 5% $CO_2$. The cDNA encoding mouse 6Ckine/SLC (m6Ckine/SLC) was cloned into the pcDNA3 vector (InVitrogen, Carlsbad, Calif.) which contains a CMV promoter. C26 colon carcinoma tumor cells (kindly provided by Mario P. Colombo, Instituto Nazionale per lo Studio e la Cura dei Tumori, Milano, Italy) were transfected with this construction using the Fugene reagent (Roche Molecular Diagnostics, Mannheim, Germany) according to the manufacturer's instructions. Single C26 clones expressing m6Ckine/SLC mRNA (C26-6 CK) were obtained after neomycin (Sigma) selection at 800 µg/ml. C26 or C26-6 CK tumor cells were injected s.c. in the right flank in 100 µl DMEM and tumor growth was monitored by palpation three times a week. For antibody depletion, 0.5 mg of anti-CD8 (clone 2.43), rat control (GL 113) purified antibodies or 200 µl rabbit anti-asialo GM1 serum (Wako Pure Chemicals, Osaka, Japan) were injected i.p. in 200 µl PBS one day before tumor inoculation, then 0.2 mg of antibodies or 100 µl anti-asialo GM1 serum were injected after three days and once a week during the course of the experiment. FIG. 10 shows that subcutaneous C26-6 CK cell injection results in significantly delayed tumor intake compared to parental tumor cells (p<0.01) by logrank analysis (A and B: C26+control vs C26-6 CK+control). Depleting CD8+ cells (A) or Natural Killer cell activity (B) with specific antibodies in vivo partially reverts the delayed tumorigenicity of the C26-6 CK tumor cells, indicating that CD8+ cells and NK cells play a role in delaying tumor growth.

Tumors were surgically removed when reaching an approximate size of 1 cm. The tumor mass was minced into small fragments and incubated in collagenase A (Roche Molecular Biochemicals) solution for 30 min at 37° C. under agitation. The suspension was then washed several times in DMEM. Staining of cell suspensions was performed in PBS+5% FCS. Prior to incubation with FITC-, biotin- or PE-labeled specific antibodies, Fc receptors were blocked using Fc-Block™ CD16/CD32 antibody (PharMingen, San Diego, Calif.). The various antibodies (all from PharMingen) used in this study were CD8β (53–5.8), CD11c (HL3), anti-MHC class II I-$A^d$/I-$E^d$ (269), CD3 (145-2C11). Biotinylated antibodies were revealed with PE-streptavidin (Becton Dickinson). Phenotypic parameters were acquired on a FacScan (Becton Dickinson, Mountain View, Calif.) and analyzed using the CellQuest software (Becton Dickinson). In FIG. 10, C26 wild-type tumors or C26-6 CK tumors expressing m6Ckine have been analyzed for CD8 T cells and CD11c+MHC classII+ dendritic cell (DC) infiltration by flow cytometry analysis of whole tumor suspension (n=7). Data show a significant recruitment of both leukocyte subsets in C26-6 CK tumors compared to C26 tumors (Student's t test). These results suggest that m6Ckine gene transfer into tumors promote both the recruitment of dendritic cells, which are essential cells to initiate immune responses, including anti-tumor responses, as well as CD8 T cells, which are effector cells of the adaptive immune response.

Figure 11A:
FIG. 11(A+B) shows that C26 colon carcinoma tumor cells engineered to express m6Ckine are less angiogenic than the parental C26 tumor.
Figure 11B:
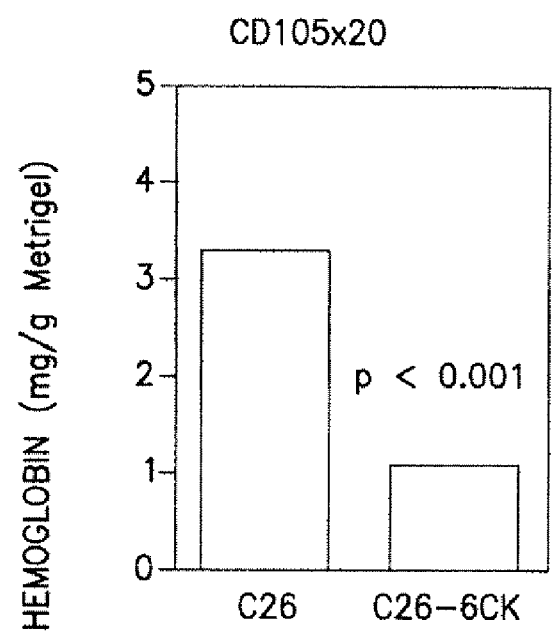

In some experiments, tumors were removed from animals and embedded in OCT compound (Miles laboratory, Elkhart, Ind.) before being snap frozen in liquid nitrogen and store at −80° C. until immunohistochemistry procedures. Five-micrometer cryostat sections applied onto glass slides were fixed in acetone and incubated with 1% $H_2O_2$ for 10 min at room temperature. Slides were then incubated with the biotin-block™ and avidin-block™ reagents (both from Vector, Burlingame, Calif.). All incubations were followed by three 2 min-washes in PBS (Gibco-BRL). Slides were then pre-incubated for 30 min with a 1/10 dilution of serum from the same species of the secondary antibody (Dako, Glostrup, Denmark). Slides were then incubated sequentially with 5 μg/ml of purified CD105 (clone MJ7/18, PharMingen, San Diego, Calif.), biotinylated secondary antibody (rabbit anti-rat from Vector), streptavidin-alkaline (ABC kit from Vector). Enzyme reaction was developed with the corresponding Vector substrate. Angiogenesis assays were carried out by determining the hemoglobin content of Matrigel (Becton Dickinson, Bedford, Mass.) pellets containing developing tumors cells in vivo. BALB/c mice were injected with 0.5 ml Matrigel mixed with $2 \times 10^5$ C26 or C26-6 CK cells s.c. in the abdominal midline. After nine days, Matrigel pellets were removed, the surrounding connective tissue was dissected away and pellets were liquefied in MatriSperse solution v/v (Becton Dickinson) for 90 min at 4° C. Hemoglobin content was determined by the Drabkin method (reagents from Sigma). FIG. 11A shows that C26-6 CK tumors are less vascularized than the parental C26 tumor. FIG. 11B shows that C26-6 CK tumor cells are less angiogenic than C26 cells in a Matrigel assay. Overall, these results indicate that gene transfer of m6Ckine chemokine into tumor has angiostatic effect on the tumor vasculature.

These results indicate that the chemokine 6Ckine could be used in cancer treatment through gene transfer. Preferred embodiments consist of but are not restricted to: DNA or viral vector (e.g. adenovirus) encoding for m6Ckine or h6Ckine or fraction of m6Ckine or h6Ckine, with or without a targeting moiety (peptide or antibody).

Example 12

Local Delivery of the Chemokine 6Ckine into Tumors in vivo

Figure 12A:
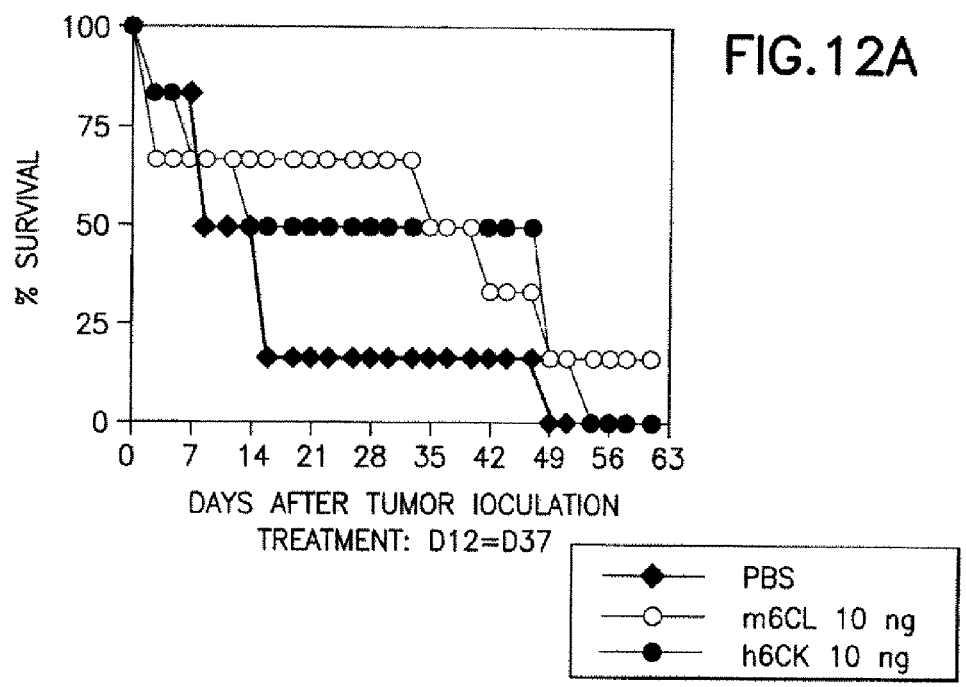
FIG. 12(A+B) shows that injection of h6Ckine slows tumor growth in mice in vivo.
Figure 12B:
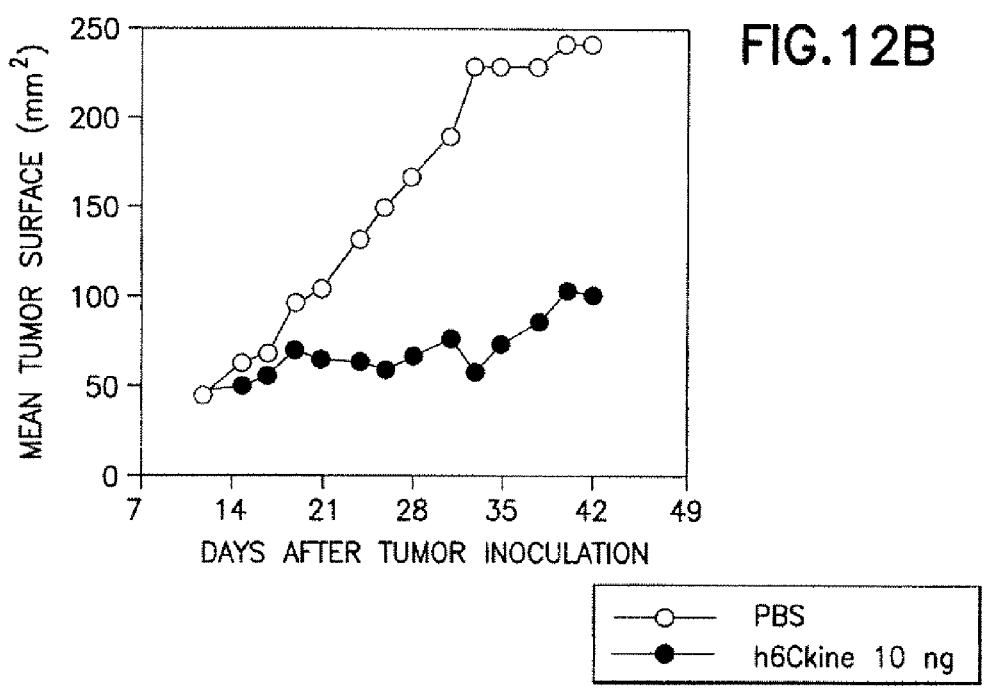

In this example, the inventors have shown that injection of recombinant human or mouse 6Ckine protein into pre-existing C26 tumors increases survival of tumor-bearing mice. Injection of h6Ckine slows tumor growth. (FIG. 12)

6- to 10-week-old female BALB/c (H-$2^d$) mice were purchased from Charles River (Iffa-Credo, L'Arbresle, France) and maintained under standard conditions. Procedures involving animals and their care were conducted in conformity with EEC (European Economic Community) Council Directive 86/609, OJL 358, 1, Dec. 12, 1987. All tumor cell cultures were performed in DMEM (Gibco-BRL, Life Technologies, Paisley Park, Scotland) supplemented with 10% FCS (Gibco-BRL), 1 mM hepes (Gibco-BRL), Gentallin (Schering-Plough, Union, N.J.), $2 \times 10^{-5}$ M beta-2 mercaptoethanol (Sigma, St Louis, Mo.). All cell cultures were performed at 37° C. in a humidified incubator with 5% $CO_2$. C26 cells were provided by Mario P. Colombo (Milano, Italy).

C26 tumor cells were injected s.c. in the right flank in 100 μl DMEM and tumor growth was monitored by palpation three times a week. In some experiments, tumor volume was monitored using a calliper and calculated as: tumor volume=small diameter$^2$×large diameter×0.4. For treatment with recombinant chemokines, mice were injected intra-tumorally with 10 ng>97% pure recombinant human or mouse 6Ckine/SLC (R&D Systems, Minneapolis, Minn.) under 50 μl PBS. FIG. 1 shows that mice injected with h6Ckine or m6Ckine show improvement in survival compared with PBS vehicle alone (A). Injection of h6Ckine also decreased the growth of tumors (B). These data show that intra-tumor delivery of recombinant 6Ckine chemokines has anti-tumor effect.

Example 13 rAd/6Ckine Mitigation of Metastatic Tumors

Female mice (BALB/c ByJ; Jackson Laboratories) were injected by subcutaneous route with $3 \times 10^{15}$ 4T1-p53 mammary tumor cells (syngeneic) in a volume of 0.2 ml (medium) into the left flank of animals. Animals received an intratumoral injection when the tumor grew to a size of 50–100 mm$^3$ of 100 μl of CMCB (1e10 PN/injection) in VPBS. Mice received 3 injections per week (Monday, Wednesday, Friday) for two weeks. The tumors were measured three times weekly using a caliper (length, width, depth), the tumor volume was calculated according to formula:

$V=4/3r^3$ where $r=(W(\text{mm})+L(\text{mm})+D(\text{mm}))$ divided by 6

Animals were sacrificed if tumors exceed 1000 mm$^3$.

3 mice from each group were sacrificed, starting at the time when the tumors reached 50 mm$^3$ (typically day 10), and the tumors and lungs were resected for tissue processing for the biochemical analyses described below and to assess the presence of metastases by gross and histological means.

Figure 13:
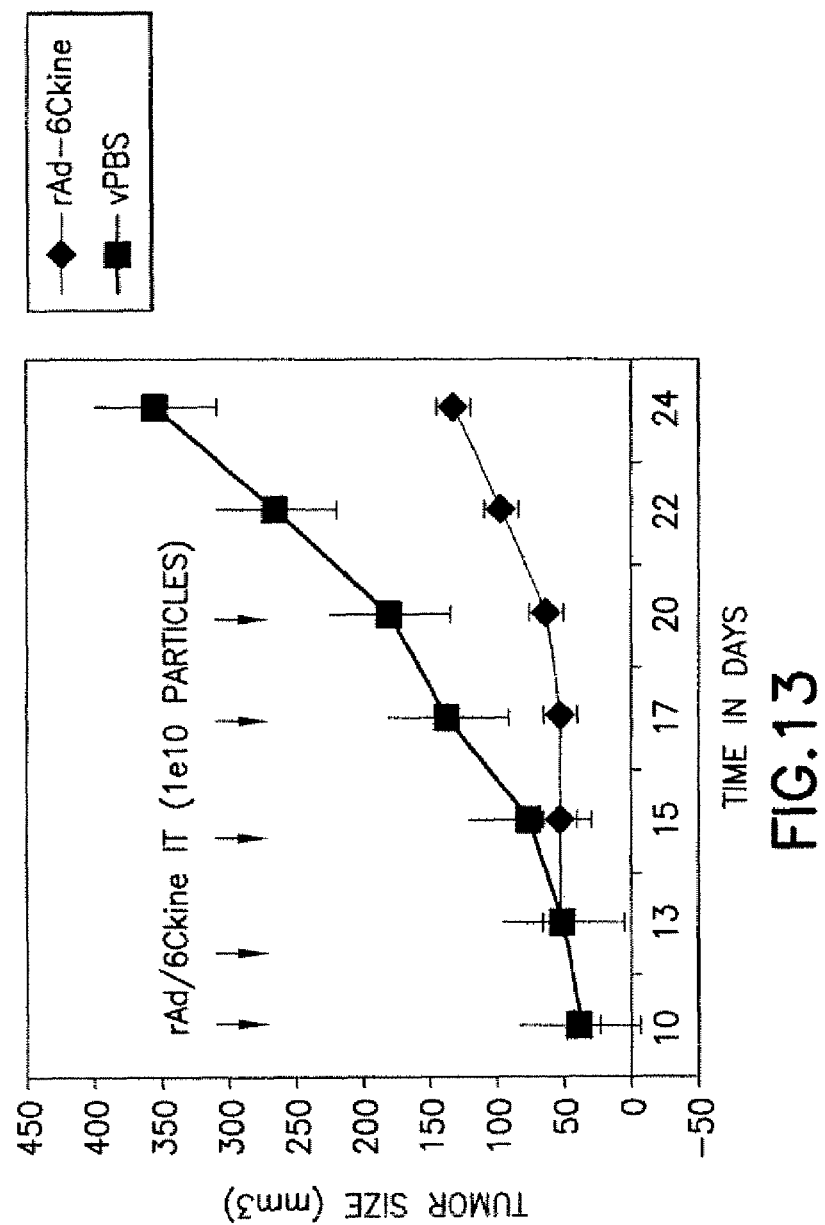
FIG. 13 shows that 6Ckine inhibits tumor growth and spontaneous metastasis in established tumors in vivo.

As shown in FIG. 13, 6Ckine inhibits tumor growth and spontaneous metastasis by in established tumors by augmenting immunity and suppressing angiogenesis.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. A method for enhancing a humoral immune response in a mammal comprising administering the protein chemokine MCP-4 and a nucleic acid encoding an antigen to said mammal, wherein said chemokine is administered prior to said nucleic acid.

2. The method of claim 1 wherein said chemokine is recombinant.

3. The method of claim 1 wherein said chemokine is human.

4. The method of claim 1 further comprising administering a substance which allows for the slow release of said chemokine at a delivery site.

5. The method of claim 1 wherein said antigen is a tumor associated antigen.

6. The method of claim 5 wherein said tumor associated antigen is selected from the group consisting of Melan-A, tyrosinase, p97, β-HCG, GaINAc., MAGE-1, MAGE-2, MAGE-3, MAGE-4, MAGE-12, MART-1, MUC1, MUC2, MUC3, MUC4, MUC18, CEA, DDC, melanoma antigen gp75, Hker 8, high molecular weight melanoma antigen, K19, Tyr1 and Tyr2, members of the pMel 17 gene family, c-Met, PSA, PSM, α-fetoprotein, thyroperoxidase, gp 100, p53 and telomerase.

7. The method of claim 1 wherein said antigen is a bacterial, viral or fungal antigen.

8. The method of claim 1 further comprising administering a combination of GM-CSF and IL-4.

9. The method of claim 1 further comprising administering a dendritic cell activating agent with said chemokine.

10. The method of claim 9 wherein the activating agent is a nucleic acid containing an unmethylated CpG motif.

11. The method of claim 1 wherein said chemokine is administered intradermally, intramuscularly, subcutaneously, or topically.

* * * * *

SEQUENCE LISTING

<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 1
atttcagcga tgttttcgac tc                                    22

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 2
ggagaagcct gaggacttgt a                                     21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 3
gattacatcg gagacaacac c                                     21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 4
tagtccaggc agaagagtcg                                       20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 5
gctgccttgg gtgttgtatt t                                     21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 6
agaggagcag cagtgagcaa                                       20

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 7
ttgctcctgg ctgctttg                                         18

<210> SEQ ID NO 8

```
-continued

<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 8
accctccatg atgtgcaag                                              19

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 9
ctgctggttc tctggacttc                                             20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 10
cacactcaca ctcacacaca c                                           21
```